US011945837B2

(12) United States Patent
Bill, Jr. et al.

(10) Patent No.: US 11,945,837 B2

(45) **Date of Patent: *Apr. 2, 2024**

(54) ION EXCHANGE MEMBRANE CHROMATOGRAPHY

(71) Applicant: Genentech, Inc., South San Francisco, CA (US)

(72) Inventors: Jerome Joseph Bill, Jr., South San Francisco, CA (US); Arick Michael Brown, South San Francisco, CA (US); Christopher John Dowd, South San Francisco, CA (US); Brooke Ellen Thayer, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 1249 days.

This patent is subject to a terminal disclaimer.

(21) Appl. No.: 16/433,763

(22) Filed: Jun. 6, 2019

(65) Prior Publication Data

US 2020/0102346 A1 Apr. 2, 2020

Related U.S. Application Data

(63) Continuation of application No. 14/365,449, filed as application No. PCT/US2012/070373 on Dec. 18, 2012, now Pat. No. 10,364,268.

(60) Provisional application No. 61/579,285, filed on Dec. 22, 2011.

(51) Int. Cl.

| | |
|---|---|
| ***C07K 1/18*** | (2006.01) |
| ***B01D 15/36*** | (2006.01) |
| ***C07K 1/16*** | (2006.01) |
| ***C07K 16/06*** | (2006.01) |

(52) U.S. Cl.

CPC ................ *C07K 1/18* (2013.01); *C07K 1/165* (2013.01); *C07K 16/065* (2013.01)

(58) Field of Classification Search

None

See application file for complete search history.

(56) References Cited

U.S. PATENT DOCUMENTS

| | | | |
|---|---|---|---|
| 3,773,919 | A | 11/1973 | Boswell |
| RE30,985 | E | 6/1982 | Cartaya |
| 4,515,893 | A | 5/1985 | Kung et al. |
| 4,560,655 | A | 12/1985 | Baker |
| 4,657,866 | A | 4/1987 | Kumar |
| 4,767,704 | A | 8/1988 | Cleveland |
| 4,816,567 | A | 3/1989 | Cabilly |
| 4,927,762 | A | 5/1990 | Darfler |
| 5,091,178 | A | 2/1992 | Hellstrom et al. |
| 5,091,313 | A | 2/1992 | Chang |
| 5,122,469 | A | 6/1992 | Mather et al. |
| 5,534,615 | A | 7/1996 | Baker et al. |
| 5,591,828 | A | 1/1997 | Bosslet |
| 5,595,721 | A | 1/1997 | Kaminski et al. |
| 5,622,700 | A | 4/1997 | Jardieu et al. |
| 5,677,180 | A | 10/1997 | Robinson et al. |
| 5,693,762 | A | 12/1997 | Queen et al. |
| 5,714,338 | A | 2/1998 | Wai Fei et al. |
| 5,725,856 | A | 3/1998 | Hudziak et al. |
| 5,736,137 | A | 4/1998 | Anderson et al. |
| 7,151,164 | B2 | 12/2006 | Hansen |
| 10,364,268 | B2 | 7/2019 | Bill, Jr. |
| 10,927,144 | B2 | 2/2021 | Brown et al. |
| 2002/0002271 | A1 | 1/2002 | Rinderknecht |
| 2002/0012982 | A1 | 1/2002 | Blakesley |

(Continued)

FOREIGN PATENT DOCUMENTS

| | | |
|---|---|---|
| AU | 2010292897 B2 | 1/2016 |
| CA | 2242931 A1 | 8/1997 |

(Continued)

OTHER PUBLICATIONS

Barnes, D. et al. (Mar. 1, 1980). "Methods for Growth of Cultured Cells In Serum-Free Medium," Anal. Biochem. 102(2):255-270.

Brennan, M. et al. (Jul. 5, 1985). "Preparation of Bispecific Antibodies by Chemical Recombination of Monoclonal Immunoglobulin G1 Fragments," Science 229:81-83.

Brown, A. (Jul. 1, 2010, e-pub. Mar. 12, 2010). "Increasing Parvovirus Filter Throughput of Monoclonal Antibodies Using Ion Exchange Membrane Adsorptive Pre-filtration," Biotechnology and Bioengineering, 106(4):627-637.

Brüggermann, M. et al. (1993). "Designer Mice: The Production Of Human Antibody Repertoires In Transgenic Animals," Year Immunology 7:33-40.

Carter, P. et al. (Feb. 1992). "High Level *Escherichia coli* Expression and Production of a Bivalent Humanized Antibody Fragment," Bio/Technology 10:163-167.

(Continued)

*Primary Examiner* — Daniel E Kolker

*Assistant Examiner* — James L Rogers

(74) *Attorney, Agent, or Firm* — Morrison & Foerster LLP

(57) ABSTRACT

Methods of enhancing efficiency of downstream chromatography steps for purification of proteins comprising: (a) passing a composition comprising a polypeptide of interest and various contaminants through an ion exchange membrane, wherein the polypeptide and the membrane have opposite charge, at operating conditions comprised of a buffer having a pH sufficiently distinct from the pi of the polypeptide to enhance the charge of the polypeptide and a low ionic strength effective to prevent the shielding of charges by buffer ions, which cause the membrane to bind the polypeptide and at least one contaminant, (b) overloading the ion exchange membrane such that at least one contaminant remains bound to the membrane while the polypeptide of interest is primarily in the effluent; (c) collecting the effluent from the ion exchange membrane comprising the polypeptide of interest; (d) subjecting the membrane effluent comprising the polypeptide of interest to a purification step of similar charge as the previous membrane, and (e) recovering the purified polypeptide from the effluent of the charged ion exchange chromatography purification step.

16 Claims, 16 Drawing Sheets

(56) References Cited

U.S. PATENT DOCUMENTS

| | | | |
|---|---|---|---|
| 2004/0093621 A1 | 5/2004 | Shitara et al. | |
| 2004/0167319 A1 | 8/2004 | Teeling et al. | |
| 2005/0025764 A1 | 2/2005 | Watkins et al. | |
| 2005/0069545 A1 | 3/2005 | Carr et al. | |
| 2008/0274501 A1 | 11/2008 | Zhang | |
| 2009/0050566 A1 | 2/2009 | Kozlov | |
| 2009/0148435 A1 | 6/2009 | Lebreton | |
| 2010/0228010 A1 | 9/2010 | Shirataki | |
| 2011/0034674 A1 | 2/2011 | Mehta | |
| 2011/0287009 A1 | 11/2011 | Scheer | |
| 2013/0079272 A1* | 3/2013 | Liu | B01D 15/3847 530/416 |
| 2014/0296485 A1 | 10/2014 | Haymore | |
| 2014/0348845 A1 | 11/2014 | Bill, Jr. | |
| 2021/0284685 A1 | 9/2021 | Brown et al. | |

FOREIGN PATENT DOCUMENTS

| | | |
|---|---|---|
| DE | DD266710 A3 | 4/1989 |
| EP | 0244234 A2 | 11/1987 |
| EP | 0402226 A1 | 12/1990 |
| EP | 0420937 A1 | 4/1991 |
| EP | 0404097 B1 | 9/1996 |
| EP | 2462158 B1 | 6/2012 |
| JP | S6150925 A | 3/1986 |
| JP | H03200797 A | 9/1991 |
| JP | H11504007 A | 4/1999 |
| JP | 2004504330 A | 2/2004 |
| KR | 1020110067099 A | 6/2011 |
| RU | 2145873 C1 | 2/2000 |
| WO | WO198700195 A1 | 1/1987 |
| WO | WO199003430 A1 | 4/1990 |
| WO | WO199304173 A1 | 3/1993 |
| WO | WO199311161 A1 | 6/1993 |
| WO | WO199316185 A2 | 8/1993 |
| WO | WO199316185 A3 | 9/1993 |
| WO | WO199519181 A1 | 7/1995 |
| WO | WO199523865 A1 | 9/1995 |
| WO | WO199630046 A1 | 10/1996 |
| WO | WO199640210 A1 | 12/1996 |
| WO | WO199726912 A2 | 7/1997 |
| WO | WO199727757 A1 | 8/1997 |
| WO | WO199726912 A3 | 10/1997 |
| WO | WO199806248 A2 | 2/1998 |
| WO | WO199806248 A3 | 5/1998 |
| WO | WO199823761 A1 | 6/1998 |
| WO | WO199845331 A2 | 10/1998 |
| WO | WO199851793 A1 | 11/1998 |
| WO | WO199845331 A3 | 12/1998 |
| WO | WO199902556 A1 | 1/1999 |
| WO | WO200075348 A1 | 12/2000 |
| WO | WO200100245 A2 | 1/2001 |
| WO | WO200140309 A2 | 6/2001 |
| WO | WO200100245 A3 | 10/2001 |
| WO | WO200140309 A3 | 11/2001 |
| WO | WO200224909 A2 | 3/2002 |
| WO | WO2003002607 A1 | 1/2003 |
| WO | WO2003025156 A2 | 3/2003 |
| WO | WO2003033656 A2 | 4/2003 |
| WO | WO200224909 A3 | 7/2003 |
| WO | WO2003025156 A3 | 8/2003 |
| WO | WO2003033656 A3 | 11/2003 |
| WO | WO2004035607 A2 | 4/2004 |
| WO | WO2004056312 A2 | 7/2004 |
| WO | WO2004035607 A3 | 8/2004 |
| WO | WO2004103404 A1 | 12/2004 |
| WO | WO2005000901 A2 | 1/2005 |
| WO | WO2005014618 A2 | 2/2005 |
| WO | WO2005016969 A2 | 2/2005 |
| WO | WO2005016969 A3 | 4/2005 |
| WO | WO2004056312 A3 | 5/2005 |
| WO | WO2005000901 A3 | 6/2005 |
| WO | WO2005014618 A3 | 3/2009 |
| WO | WO2009054226 A1 | 4/2009 |
| WO | WO2009135656 A1 | 11/2009 |
| WO | WO2010019148 A1 | 2/2010 |
| WO | WO2010026432 A1 | 3/2010 |
| WO | WO2011028753 A1 | 3/2011 |
| WO | WO2011031397 A1 | 3/2011 |
| WO | WO2011150110 A1 | 12/2011 |

OTHER PUBLICATIONS

Carter, P. et al. (May 1992). "Humanization of An Anti-p185HER2 Antibody For Human Cancer Therapy," Proc. Natl. Acad. Sci. USA 89:4285-4289.

Ceriani, R.L. et al. (Dec. 1, 1995). "Biological Activity of Two Humanized Antibodies Against Two Different Breast Cancer Antigens and Comparison to Their Original Murine Forms," Cancer Res. 55(23):5852s-5856s.

Chothia, C. et al. (1987). "Canonical Structures for the Hypervariable Regions of Immunoglobulins," J. Mol. Biol. 196:901-917.

Choy, E.H.S. et al. (Jan. 1996). "Percentage of Anti-CD4 Monoclonal Antibody-Coated Lymphocytes in the Rheumatoid Joint is Associated With Clinical Improvement," Arthritis Rheum 39(1):52-56.

Clackson, T. et al. (Aug. 15, 1991). "Making Antibody Fragments Using Phage Display Libraries," Nature 352:624-628.

Cragg, M.S., et al. (2003). "Complement-Mediated Lysis By Anti-CD20 Mab Correlates With Segregation Into Lipid Rafts," Blood 101:1045-1052.

Drager, R.R. et al. (1986). "Application of The Stoichiometric Displacement Model Of Retention To Anion-Exchange Chromatography Of Nucleic Acids," J Chromatogr. 359:147-155.

Duchosal, M.A. et al. (1992). "Immunization Of Hu-PBL-SCID Mice and The Rescue Of Human Monoclonal Fab Fragments Through Combinatorial Libraries," Nature 355:258-262.

Ellis, J.H. et al. (1995). "Engineered Anti-CD38 Monoclonal Antibodies for Immunotherapy of Multiple Myeloma," J. Immunol. 155(2):925-937.

European Search Report dated Apr. 12, 2019, for European Patent Application No. 18193475.3, 7 pages.

Fahrner, R.L. et al. (2001). "Industrial purification Of Pharmaceutical Antibodies: Development, Operation and Validation Of Chromatography Processes," Biotechnol .Genet. Eng. Rev. 18:301-327.

Freitag, R. et al. (1995). "Displacement Chromatography In Biotechnological Downstream Processing," J. Chromatogr. A 691(1-2):101-112.

Freitag, R. (2003). "Novel Approaches To The Chromatography Of Proteins," Biotechnology and Bioprocessing/ Biotechnol. Bioprocess. 27:455-502.

Glennie, M.J. et al. (2003). "Renaissance Of Cancer Therapeutic Antibodies," Drug Discovery Today 8:503-510.

Graham, F.L. et al. (1977). "Characteristics Of A Human Cell Line Transformed By DNA From Human Adenovirus Type 5," Journal General Virology 36(1 ):59-74.

Graziano, R.F. et al. (1995). "Construction and Characterization of a Humanized Anti-γ-Ig Receptor Type I (FcγRI) Monoclonal Antibody," J. Immunol. 155(10):4996-5002.

Haisma, H.J. et al. (1998). "Construction and Characterization Of A Fusion Protein Of Single-Chain Anti-CD20 Antibody and Human β-Glucuronidase For Antibody-Directed Enzyme Prodrug Therapy," Blood 92(1):184-190.

Ham, R.J. et al. (1979). "Media and Growth Requirements," Meth. Enz. 58:44-93.

Holliger, P. et al. (Jul. 1993). ""Diabodies"": Small Bivalent and Bispecific Antibody Fragments, Proceedings of the National Academy of Sciences USA 90:6444-6448.

Horie, K. et al. (2004). "Definitions Of Terms Relating To Reactions Of Polymers and To Functional Polymeric Materials," Pure Appl. Chem. 76(4):889-906.

Hourmant, M. et al. (Aug. 1994). "Administration of An Anti-CD11a Monoclonal Antibody in Recipients of Kidney Transplantation: A Pilot Study," Transplantation 58:377-380.

Ibidapo, T.A. (Nov. 1988). "Classification Of Ionic Polymers," Polymer Engineering and Science 22:1473-1476.

(56) References Cited

OTHER PUBLICATIONS

International Preliminary Report On Patentability, dated Jun. 24, 2014, for PCT Application No. PCT/US2012/070373, filed Dec. 18, 2012, 5 pages.
International Search Report, dated Apr. 29, 2013, for PCT Application No. PCT/US2012/070373, filed Dec. 18, 2012, 3 pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
Juricic, J.G. et al. (1995). "Radiolabeled Anti-CD33 Monoclonal Antibody MI95 For Myeloid Leukemias," Cancer Research 55:5908s-5910s.
Kim, K.J. et al. (1992). "The Vascular Endothelial Growth Factor Proteins: Identification Of Biologically Relevant Regions By Neutralizing Monoclonal Antibodies," Growth Factors 7:53-64.
Köhler, G. et al. (Aug. 7, 1975). "Continuous Cultures of Fused Cells Secreting Antibody of Predefined Specificity," Nature 256:495-497.
Litton, M.J. et al. (1996). "Antibody-Targeted Superantigen Therapy Induces Tumor-Infiltrating Lymphocytes, Excessive Cytokine Production, and Apoptosis in Human Colon Carcinoma," Eur J. Immunol. 26(1): 1-9.
Marks, J.D. et al. (1991). "By-Passing Immunization. Human Antibodies From V-Gene Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10: 779-783.
Mather, J.P. et al. (1980). "Establishment and Characterization Of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals N.Y. Acad. Sci. 383:44-68.
McCafferty, J. et al. (Dec. 6, 1990). "Phage Antibodies: Filamentous Phage Displaying Antibody Variable Domains," Nature 348:552-554.
Morimoto, K. et al. (1992). "Single-Step Purification of F(ab')2 Fragments of Mouse Monoclonal Antibodies (Immunoglobulins G1) by Hydrophobic Interaction High Performance Liquid Chromatography Using TSKgell Pheny-5PW," Journal of Biochemical and Biophysical Methods 24:107-117.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Plückthun, A. (1994). "Antibodies from *Escherichia coli*," in Chapter 11 The Pharmacology of Monoclonal Antibodies, vol. 113, Rosenburg and Moore eds., SpringerVerlag, New York, pp. 269-315.
Press, O.W. et al. (1987). "Monoclonal Antibody 1F5(Anti-CD20) Serotherapy Of Human B Cell Lymphomas," Blood 69(2):584-591.
Presta, L.G. et al. (Sep. 1, 1993). "Humanization of an Antibody Directed Against IgE," J. Immunol. 151(5):2623-2632.
Richman, C.M. et al. (Dec. 1, 1995). "Radioimmunotherapy for Breast Cancer Using Escalating Fractionated Doses of 131I-Labeled Chimeric L6 Antibody with Peripheral Blood Progenitor Cell Transfusions," Cancer Res. 55(23 Supp):5916s-5920s.
Riechmann, L. et al. (Mar. 24, 1988). "Reshaping Human Antibodies for Therapy," Nature 332:323-327.
Schmidt, B. et al. (2003). "Investigation Of Particle-Based And Monolithic Columns For Cation Exchange Protein Displacement Chromatography Using Poly(diallyl-dimethylammonium chloride) As Displacer," J. Chromatography A 1018:155-167.
Sharkey, R.M. et al. (Dec. 1, 1995). "Evaluation of a Complementarity-Determining Region-Grafted (Humanized) Anti-Carcinoembryonic Antigen Monoclonal Antibody in Preclinical and Clinical Studies," Cancer Res. 55 (23Suppl):5935s-5945s.
Sims, M.J. et al. (Aug. 15, 1993). "A Humanized CD18 Antibody Can Block Function Withoud Cell Destruction," J. Immunol. 151:2296-2308.
St John, R.C. et al. (Mar. 1993). "Immunologic Therapy For ARDS, Septic Shock, And Multiple-Organ Failure," Chest 103(3):932-943.
Stoppa, A.M. et al. (Apr. 1991). "Anti-LFA1 Monoclonal Antibody (25.3) For Treatment Of Steroid-Resistant Grade III-IV Acute Graft-Versus-Host Disease," Transplant Intl. 4(1):3-7.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Waterhouse, P. et al. (1993). "Combinatorial Infection and in Vivo Recombination: a Strategy for Making Large Phage Antibody Repertoires," Nucl. Acids Res., 21(9):2265-2266.
Written Opinion Of The International Search Report, dated Apr. 29, 2013, for PCT Application No. PCT/US2012/070373, filed Dec. 18, 2012, 4 pages.
Zapata, G. et al. (1995). "Engineering Linear F(ab')2 Fragments For Efficient Production In *Escherichia coli* And Enhanced Antiproliferative Activity," Protein Engineering 8(10):1057-1062.

* cited by examiner

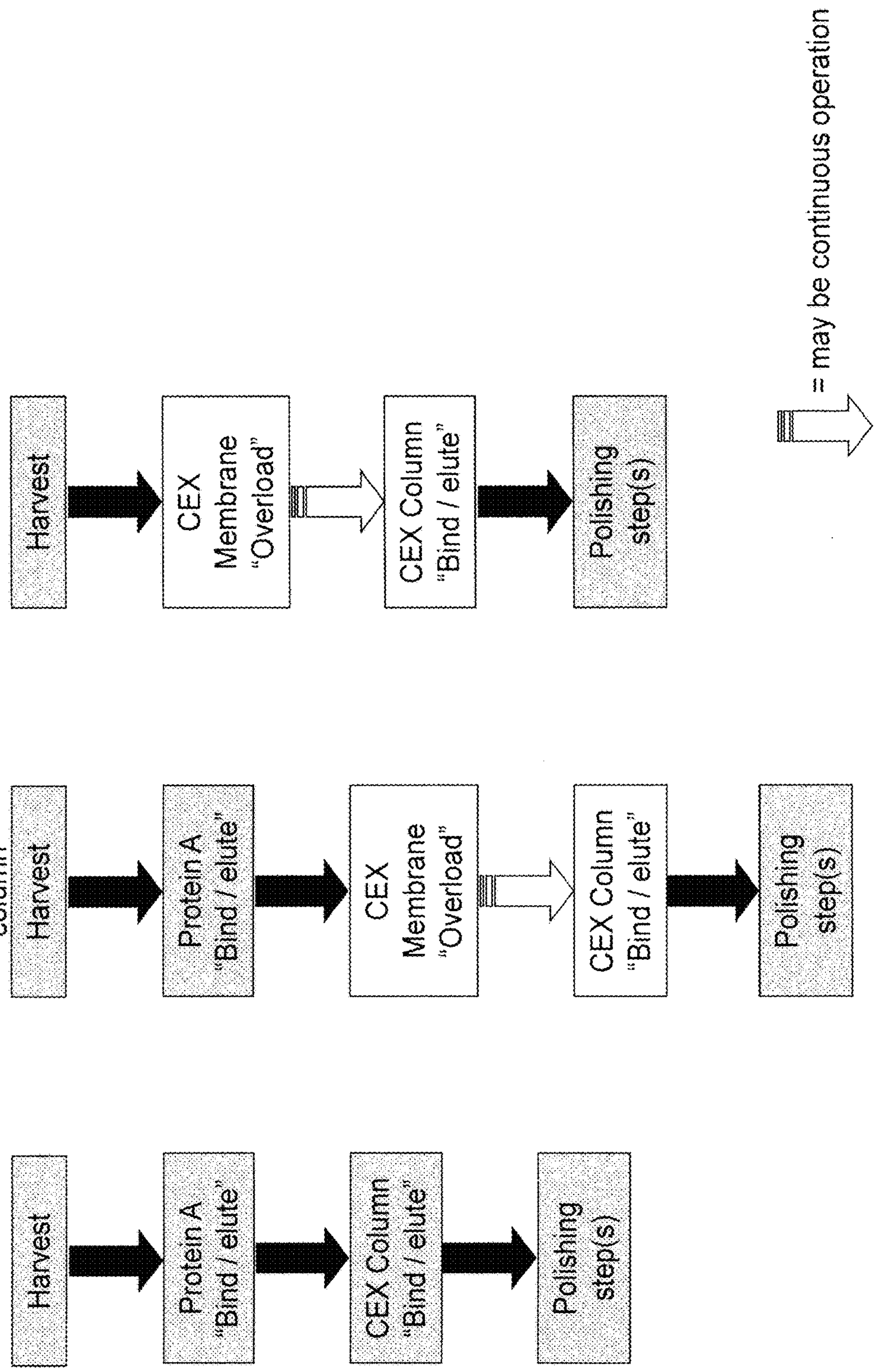
Figure 1
Traditional antibody purification with Protein A capture step
Harvest
Protein A "Bind / elute"
CEX Column "Bind / elute"
Polishing step(s)
Antibody purification with Protein A capture, CEX membrane protecting CEX column
Harvest
Protein A "Bind / elute"
CEX Membrane "Overload"
CEX Column "Bind / elute"
Polishing step(s)
Antibody purification with CEX membrane protecting CEX capture step
Harvest
CEX Membrane "Overload"
CEX Column "Bind / elute"
Polishing step(s)
= may be continuous operation Traditional non-antibody purification with CEX capture step
Harvest
CEX Column "Bind / elute"
Polishing step(s)
Traditional non-antibody purification wtih CEX membrane protecting CEX capture step
Harvest
CEX Membrane "Overload"
CEX Column "Bind / elute"
Polishing step(s)
= may be continuous operation Yield (%)
Load Density (g/L)
4 mS/cm
7 mS/cm
10 mS/cm
0
10
20
30
40
50
60
70
80
90
100
200
400
600
800
1,000
1,200

Monomer
Dimer
HMWS
CHOP
Gentamicin
LMWS
% Normalized Mass
100
75
50
25
0
1
5
10
15
Load Density (kg/L m)

Mustang S Acrodisc
1333 MV/hr

Wash Buffer
20mM Acetate
pH 5.4, 1.9 mS/cm

Elution Buffer
Wash + 2 mg/mL Gent.
pH 5.4, 1.9 mS/cm

| | Load | mAb (mg/mL) | Gentamicin (ng/mL) | CHOP (ng/mL) | DBC (g/L) | Exp. Order |
|---|---|---|---|---|---|---|
| ■ | Adj. HCCF 1 | 0.89 | 24,100 | 408,000 | 68 | 4th |
| ◆ | Adj. HCCF 2 | 0.87 | 30,000 | | 71 | 1st |
| ● | Pure mAb | 1.62 | 30,500 | 0 | 88 | 3rd |
| ▲ | Pure mAb | 1.64 | 24,100 | | 89 | 5th |
| X | Pure mAb | 1.64 | 0 | | 108 | 2nd |

| | Adj. HCCF | Natrix flow-through |
|---|---|---|
| mAb (mg/mL) | 0.88 | 0.83 |
| CHOP (ng/mL) | 408,000 | 328,000 |
| Gent. (ng/mL) | 24,100 | 870 |

| Load | Target protein (mg/mL) | ECP (ng/mL) | PEI (µg/mL) |
|---|---|---|---|
| Protein A pool | 4.7 | 8,870 | 130 |

| Run | 40 | 44 | 45 | 46 |
|---|---|---|---|---|
| Pre-Harvest PEI added (%) | 0.75 | 0.85% | 0.95% | 1.05% |
| Dynamic Binding Capacity (g/L) at 10% break-through | 51 | 49 | 43 | 36 |

Figure 16

| Run | Pre-Harvest Condition | Load Protein (mg/mL) | SP Sepharose Fast Flow | | | |
|---|---|---|---|---|---|---|
| | | | Step Yield (%) | Pool ECP (ng/mg) | Pool Aggregate (%) | Pool Dimer (%) |
| | *Effect of PEI concentration* | | | | | |
| 29 | 0.60% PEI | 6.9 | 88 | 155 | 2.5 | 3.7 |
| | 0.70% PEI | 6.6 | 96 | 145 | 7.5 | 3.8 |
| | 0.80% PEI | 7.3 | 93 | 247 | 5.4 | 3.4 |
| | 0.90% PEI | 7.5 | 91 | 274 | 3.5 | 3.3 |
| | 1.00% PEI | 7.3 | 81 | 621 | 6.8 | 5.0 |
| | 1.10% PEI | 7.4 | 70 | 904 | 17.3 | 5.9 |

ION EXCHANGE MEMBRANE CHROMATOGRAPHY

CROSS-REFERENCE TO RELATED APPLICATIONS

This application is a continuation of U.S. patent application Ser. No. 14/365,449, which adopts the international filing date of Dec. 18, 2012, which is a U.S. national phase application under 35 U.S.C. § 371 of International Application No. PCT/US2012/070373, filed on Dec. 18, 2012, which claims the priority benefit of U.S. Provisional Application No. 61/579,285, filed on Dec. 22, 2011.

FIELD OF THE INVENTION

This invention relates generally to protein purification. In particular, the invention relates to methods for improving the performance of downstream purification steps to remove impurities through the use of upstream ion exchange membrane chromatography.

BACKGROUND OF THE INVENTION

The large-scale, economic purification of proteins is an increasingly important problem for the biotechnology industry. Generally, proteins are produced by cell culture, using either eukaryotic or prokaryotic cell lines engineered to produce the protein of interest by insertion of a recombinant plasmid containing the gene for that protein. These cells must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the mechanism of expression for the given protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest without large cellular debris components has been obtained, its separation from the remaining other proteins produced by the cell is usually attempted using a combination of different chromatography techniques. These techniques separate mixtures of proteins and other impurities on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted or displaced by different solvents or displacers. In some cases, the desired protein is separated from impurities when the impurities specifically adhere to the column, and the protein of interest does not, that is, the protein of interest is present in the "flow-through". Publications concerning protein purification include Fahrner et al., Biotechnol Genet Eng Rev. 2001; 18:301-27.

A typical large-scale purification process for antibodies is often built around the employment of immobilized protein A as the primary capture and purification step in combination with other column operations. Protein A is a cell wall protein from *Staphylococcus aureas* with affinity for the Fc region of IgG. For this reason it is used extensively for IgG purification. Protein A column operations in general deliver a product-related purity over 98% with most process impurities washed away in the flow-through fraction. However, there are numerous drawbacks to the use of Protein A chromatography. First, binding is usually done at a neutral to slightly basic pH and elution is usually at an acidic pH. One of the potential problems is that low pH can denature or partially denature the IgG. Because of this and the high product purity required for clinical applications, additional concentrating and purifying steps are required for separation of product-related isomers and removal of remaining amounts of host cell proteins/DNA, cell culturing impurities, leached protein A, and viruses. A compounding problem is that many of these impurities can interfere with the efficiency of downstream process operational units for isolating purified antibodies. Another main problem is price; Protein A columns are far more expensive than conventional ion exchange columns. Finally, there are numerous scenarios where Protein A chromatography is either not suitable or cost prohibitive, for example with the purification of polypeptides, antibody-like molecules, antibody fragments, and/or full antibodies purified from certain cell systems.

The nature of the present invention addresses the above identified problems and in its embodiments demonstrate an alternative purification method to those currently available in the art using a Protein A step in antibody, antibody fragment and polypeptide purification.

SUMMARY OF THE INVENTION

The invention herein concerns methods for enhancing efficiency of downstream chromatography steps for purification of proteins comprising (a) passing a composition comprising a polypeptide of interest and various contaminants through an ion exchange membrane, wherein the polypeptide and the membrane have opposite charge, at operating conditions comprised of a buffer having a pH sufficiently distinct from the pI of the polypeptide to enhance the charge of the polypeptide and a low ionic strength effective to prevent the shielding of charges by buffer ions, which cause the membrane to bind the polypeptide and the at least one contaminant, (b) collecting a fraction from the ion exchange membrane comprising the polypeptide of interest; (c) subjecting the composition comprising the polypeptide to one or more further purification step(s), and (d) recovering the purified polypeptide from the effluent.

In one alternative, the invention concerns a method of enhancing efficiency of downstream chromatography steps for purification of proteins comprising (a) passing a composition comprising a polypeptide of interest and various contaminants through a cation exchange membrane, where the polypeptide and the membrane have opposite charge, at operating conditions comprised of a buffer having a pH of about 1 to about 5 pH units below the pI of the polypeptide and a conductivity of ≤ about 40 mS/cm, which cause the membrane to bind the polypeptide and the at least one contaminant, and (b) collecting a fraction from the ion exchange membrane comprising the polypeptide of interest; (c) subjecting the composition comprising the polypeptide to one or more further purification step(s), and (d) recovering the purified polypeptide from the effluent.

In another alternative, the invention concerns a method of enhancing efficiency of downstream chromatography steps for purification of proteins comprising (a) passing a composition comprising a polypeptide of interest and various contaminants through an anion exchange membrane, where the polypeptide and the membrane have opposite charge, at operating conditions comprised of a buffer having a pH of about 1 to about 5 pH units above the pI of the polypeptide and a conductivity of ≤ about 40 mS/cm, which cause the membrane to bind the polypeptide and the at least one contaminant, and (b) collecting a fraction from the ion exchange membrane comprising the polypeptide of interest; (c) subjecting the composition comprising the polypeptide to one or more further purification step(s), and (d) recovering the purified polypeptide from the effluent.

In one aspect, the contaminant is a Chinese Hamster Ovary Protein (CHOP). In another aspect, the contaminant is an *E. coli* Protein (ECP). In another aspect, the contaminant is gentamicin. In still another aspect, the contaminant is polyethyleneimine (PEI).

In one aspect the polypeptide comprises a CH2/CH3 region. In another aspect, the polypeptide is an antibody. In still another aspect, the antibody is a monoclonal antibody.

In other aspects, the methods further comprise subjecting the composition comprising the polypeptide to one or more further purification step(s) either before, during, or after steps a through b described above, the purification step being, in one alternative, Fc-binding affinity chromatography (e.g. Protein A chromatography) and, in another alternative, ion exchange chromatography, using a column or membrane operated in bind/elute, flow-through, or displacement mode. In still another aspect the ion exchange membrane is replaced by a monolith or depth filter.

In addition, the invention provides the preparation of a pharmaceutical composition by combining the purified polypeptide with a pharmaceutically acceptable carrier.

BRIEF DESCRIPTION OF THE DRAWINGS

FIG. 1. Outline of antibody purification by using a CEX membrane to protect a CEX column, with or without an initial protein A column.

FIG. 16. Natrix S DBC of protein, ECP, and PEI showing PEI breakthrough at 330 mg/mL membrane compared to protein and ECP breakthrough at 123 mg/mL membrane.

DETAILED DESCRIPTION OF THE PREFERRED EMBODIMENT

Definitions

Figure 2:
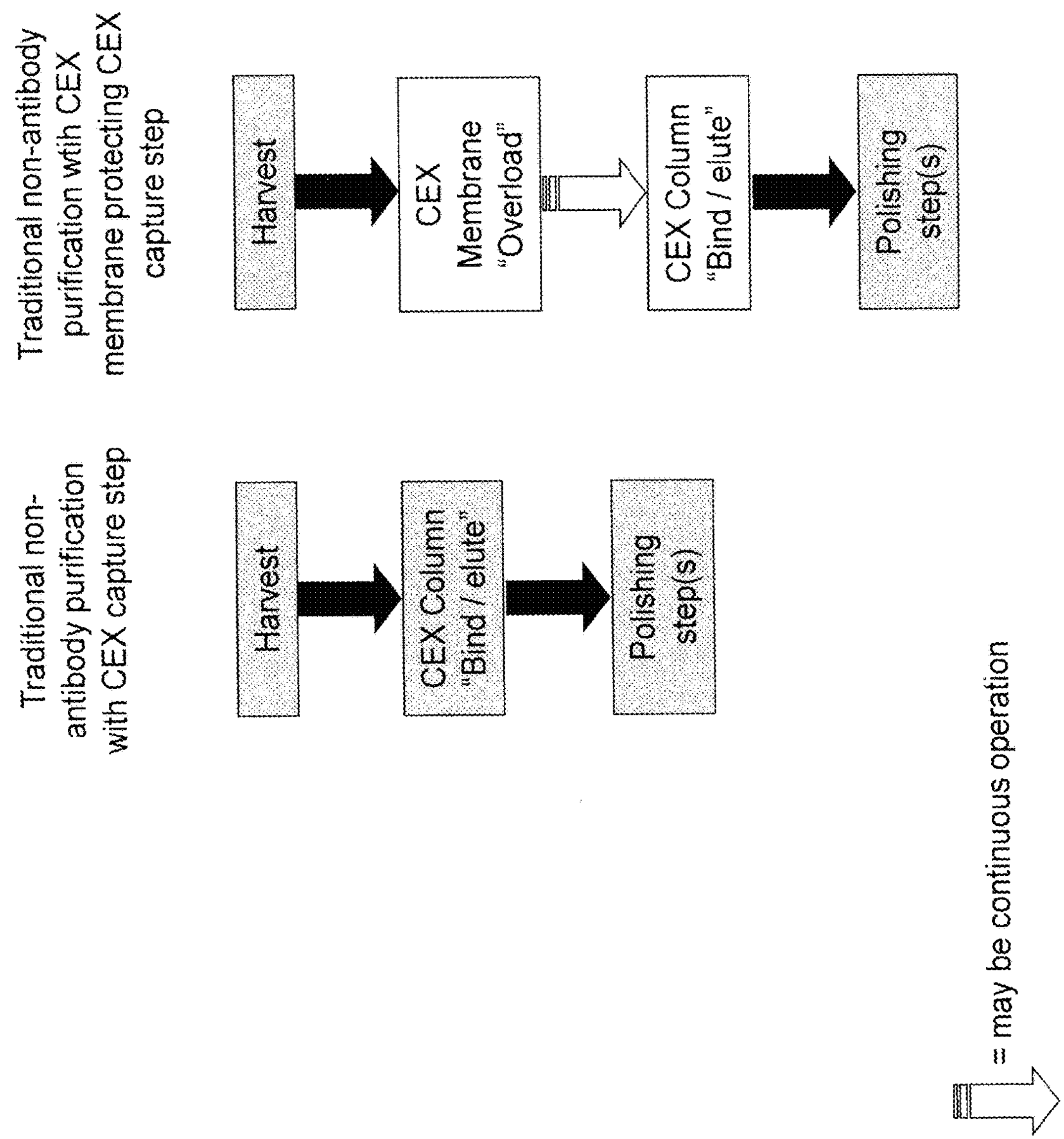
FIG. 2. Outline of non-antibody purification using a CEX membrane to protect a CEX column as the initial step.

Herein, numerical ranges or amounts prefaced by the term "about" expressly include the exact range or exact numerical amount.

The "composition" to be purified herein comprises the polypeptide of interest and one or more contaminants. The composition may be "partially purified" (i.e., having been subjected to one or more purification steps, such as protein A chromatography) or may be obtained directly from a host cell or organism producing the polypeptide (e.g., the composition may comprise harvested cell culture fluid).

As used herein, "polypeptide" refers generally to peptides and proteins having more than about ten amino acids. Preferably, the polypeptide is a mammalian protein, examples of which include: renin; a growth hormone, including human growth hormone and bovine growth hormone; growth hormone releasing factor, parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-ccll expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-1 (brain IGF-I), insulin-like growth factor binding proteins (IGFBPs); CD proteins such as CD3, CD4, CD8, CDI9 and CD20; crythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interlcukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments and/or variants of any of the above-listed polypeptides as well as antibodies, including antibody fragments, binding to any of the above-listed polypeptides.

A "contaminant" is a material that is different from the desired polypeptide product. The contaminant includes, without limitation: host cell materials, such as Chinese Hamster Ovary Proteins (CHOP) or *E. coli* Proteins (ECP); leached protein A; nucleic acid; a variant, fragment, aggregate, isomer or derivative of the desired polypeptide; another polypeptide; endotoxin; viral contaminant; aminoglycoside antibiotic components (e.g., gentamicin, streptomycin, neomycin, kanamycin); or an ionic polymer added to the purification process (e.g., polyethyleneimine (PEI), polyvinylamine, polyarginine, polyvinylsulfonic acid, polyacrylic acid), etc.

The term "$C_H2/C_H3$ region" when used herein refers to those amino acid residues in the Fc region of an immunoglobulin molecule. In preferred embodiments, the $C_H2/C_H3$ region comprises an intact $C_H2$ region followed by an intact $C_H3$ region, and most preferably a Fc region of an immunoglobulin. Examples of $C_H2/C_H3$ region-containing polypeptides include antibodies, immunoadhesins and fusion proteins comprising a polypeptide of interest fused to, or conjugated with, a $C_H2/C_H3$ region.

In preferred embodiments of the invention, the antibody to be purified herein is a recombinant antibody. A "recombinant antibody" is one which has been produced in a host cell which has been transformed or transfected with nucleic acid encoding the antibody, or produces the antibody as a result of homologous recombination. "Transformation" and "transfection" are used interchangeably to refer to the process of introducing nucleic acid into a cell. Following transformation or transfection, the nucleic acid may integrate into the host cell genome, or may exist as an extrachromosomal element. The "host cell" includes a cell in in vitro cell culture as well as a cell within a host animal. Methods for recombinant production of polypeptides are described in U.S. Pat. No. 5,534,615, expressly incorporated herein by reference, for example.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they retain, or are modified to comprise, a $C_H2/C_H3$ region as herein defined.

The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens (such as tumor-associated glycolipid antigens; see U.S. Pat. No. 5,091,178) are also contemplated. Where the antigen is a polypeptide, it may be a transmembrane molecule (e.g., receptor) or ligand such as a growth factor. Exemplary antigens include those polypeptides discussed above. Preferred molecular targets for antibodies encompassed by the present invention include CD polypeptides such as CD3, CD4, CD8, CD19, CD20 and CD34; members of the HER receptor family such as the EGF receptor (HER1), HER2, HER3 or HER4 receptor, cell adhesion molecules such as LFA-1, Mac1, p150,95, VLA-4, ICAM-1, VCAM and av/b3 integrin including either a or b subunits thereof (e.g., anti-CD11a, anti-CD18 or anti-CD11b antibodies); growth factors such as VEGF; IgE; blood group antigens; flk2/flt3 receptor; obesity (OB) receptor; mpl receptor; CTLA-4; polypeptide C etc. Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule.

Examples of antibodies to be purified herein include, but are not limited to: HER2 antibodies including trastuzumab (HERCEPTIN®) (Carter et al., *Proc. Natl. Acad. Sci. USA,* 89:4285-4289 (1992), U.S. Pat. No. 5,725,856) and pertuzumab (OMNITARG™) (WO01/00245); CD20 antibodies (see below); IL-8 antibodies (St John et al., *Chest,* 103:932 (1993), and International Publication No. WO 95/23865); VEGF or VEGF receptor antibodies including humanized and/or affinity matured VEGF antibodies such as the humanized VEGF antibody huA4.6.1 bevacizumab (AVASTIN®) and ranibizumab (LUCENTIS®) (Kim et al., *Growth Factors,* 7:53-64 (1992), International Publication No. WO 96/30046, and WO 98/45331, published Oct. 15, 1998); PSCA antibodies (WO01/40309); CD11a antibodies including efalizumab (RAPTIVA®) (U.S. Pat. No. 5,622,700, WO 98/23761, Steppe et al., *Transplant Intl.* 4:3-7 (1991), and Hourmant et al., *Transplantation* 58:377-380 (1994)); antibodies that bind IgE including omalizumab (XOLAIR®) (Presta et al., *J. Immunol.* 151:2623-2632 (1993), and International Publication No. WO 95/19181; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); CD18 antibodies (U.S. Pat. No. 5,622,700, issued Apr. 22, 1997, or as in WO 97/26912, published Jul. 31, 1997); Apo-2 receptor antibody antibodies (WO 98/51793 published Nov. 19, 1998); Tissue Factor (TF) antibodies (European Patent No. 0 420 937 B1 granted Nov. 9, 1994); $\alpha_4$-$\alpha_7$ integrin antibodies (WO 98/06248 published Feb. 19, 1998); EGFR antibodies (e.g., chimerized or humanized 225 antibody, cetuximab, ERBUTIX® as in WO 96/40210 published Dec. 19, 1996); CD3 antibodies such as OKT3 (U.S. Pat. No. 4,515,893 issued May 7, 1985); CD25 or Tac antibodies such as CHI-621 (SIMULECT®) and ZENAPAX® (See U.S. Pat. No. 5,693,762 issued Dec. 2, 1997); CD4 antibodies such as the cM-7412 antibody (Choy et al., *Arthritis Rheum* 39(1):52-56 (1996)); CD52 antibodies such as CAMPATH-1H (ILEX/Berlex) (Riechmann et al., *Nature* 332: 323-337 (1988)); Fc receptor antibodies such as the M22 antibody directed against Fc(RI as in Graziano et al., *J. Immunol.* 155(10):4996-5002 (1995)); carcinoembryonic antigen (CEA) antibodies such as hMN-14 (Sharkey et al., *Cancer Res.* 55(23Suppl): 5935s-5945s (1995)); antibodies directed against breast epithelial cells including huBrE-3, hu-Mc 3 and CHL6 (Ceriani et al., *Cancer Res.* 55(23): 5852s-5856s (1995); and Richman et al., *Cancer Res.* 55(23 Supp): 5916s-5920s (1995)); antibodies that bind to colon carcinoma cells such as C242 (Litton et al., *Eur J. Immunol.* 26(1):1-9 (1996)); CD38 antibodies, e.g., AT 13/5 (Ellis et al., *J. Immunol.* 155(2):925-937 (1995)); CD33 antibodies such as Hu M195 (Jurcic et al., *Cancer Res* 55(23 Suppl): 5908s-5910s (1995)) and CMA-676 or CDP771; EpCAM antibodies such as 17-LA (PANOREX®); Gpllb/llla antibodies such as abciximab or c7E3 Fab (REOPRO®); RSV antibodies such as MEDI-493 (SYNAGIS®); CMV antibodies such as PROTOVIR®; HIV antibodies such as PRO542; hepatitis antibodies such as the Hep B antibody OSTAVIR®; CA 125 antibody OvaRex; idiotypic GD3 epitope antibody BEC2; αvβ3 antibody (e.g., VITAXIN®; Medimmune); human renal cell carcinoma antibody such as ch-G250; ING-1; anti-human 17-1An antibody (3622W94); anti-human colorectal tumor antibody (A33); anti-human melanoma antibody R24 directed against GD3 ganglioside; anti-human squamous-cell carcinoma (SF-25); human leukocyte antigen (HLA) antibody such as Smart ID10 and the anti-HLA DR antibody Oncolym (Lym-1); CD37 antibody such as TRU 016 (Trubion); IL-21 antibody (Zymogenetics/ Novo Nordisk); anti-B cell antibody (Impheron); B cell targeting MAb (Immunogen/Aventis); ID09C3 (Morphosys/ GPC); LymphoRad 131 (HGS); Lym-1 antibody, such as Lym-1Y-90 (USC) or anti-Lym-1 Oncolym (USC/Peregrine); LIF 226 (Enhanced Lifcsci.); BAFF antibody (e.g., WO 03/33658); BAFF receptor antibody (see e.g., WO 02/24909); BR3 antibody; Blys antibody such as belimumab; LYMPHOSTAT-B™; ISF 154 (UCSD/Roche/Tragen); gomilixima (Idec 152; Biogen Idec); IL-6 receptor antibody such as atlizumab (ACTEMRA™; Chugai/Roche); IL-15 antibody such as HuMax-II-15 (Genmab/Amgen); chemokine receptor antibody, such as a CCR2 antibody (e.g., MLN 1202; Millieneum); anti-complement antibody, such as C5 antibody (e.g., eculizumab, 5G1.1; Alexion); oral formulation of human immunoglobulin (e.g., IgPO; Protein Therapeutics); IL-12 antibody such as ABT-874 (CAT/Abbott); Teneliximab (BMS-224818; BMS); CD40 antibodies, including S2C6 and humanized variants thereof (WO00/ 75348) and TNX 100 (Chiron/Tanox); TNF-α antibodies including cA2 or infliximab (REMICADE®), CDP571, MAK-195, adalimumab (HUMIRA™), pegylated TNF-α antibody fragment such as CDP-870 (Celltech), D2E7 (Knoll), anti-TNF-α polyclonal antibody (e.g., PassTNF; Verigen); CD22 antibodies such as LL2 or epratuzumab (LYMPHOCIDE®; Immunomedics), including epratuzumab Y-90 and epratzumab I-131, Abiogen's CD22 antibody (Abiogen, Italy), CMC 544 (Wyeth/Celltech), combotox (UT Soutwestem), BL22 (NIH), and LympoScan Tc99 (Immunomedics).

Examples of CD20 antibodies include: "C2B8," which is now called "rituximab" ("RITUXAN®") (U.S. Pat. No. 5,736,137); the yttrium-[90]-labelled 2B8 murine antibody designated "Y2B8" or "Ibritumomab Tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine 1131 tositumomab" antibody (BEXXAR™) commercially available from Corixa (see, also, U.S. Pat. No. 5,595,721); murine monoclonal antibody "IF5" (Press et al., *Blood* 69(2):584-591 (1987)) and variants thereof including "framework patched" or humanized 1F5 (WO 2003/002607, Leung, S.; ATCC deposit HB-96450); murine 2H7 and chimeric 2H7 antibody (U.S. Pat. No. 5,677,180); humanized 2H7 (WO 2004/056312, Lowman et al.,); 2F2 (HuMax-CD20), a fully human, high-affinity antibody targeted at the CD20 molecule in the cell membrane of B-cells (Genmab, Denmark; see, for example, Glennie and van de Winkel, *Drug Discovery Today* 8: 503-510 (2003) and Cragg et al., *Blood* 101: 1045-1052 (2003); WO 2004/035607; US2004/0167319); the human monoclonal antibodies set forth in WO 2004/035607 and US2004/0167319 (Teeling et al.,); the antibodies having complex N-glycoside-linked sugar chains bound to the Fc region described in US 2004/0093621 (Shitara el al.,); monoclonal antibodies and antigen-binding fragments binding to CD20 (WO 2005/000901, Tedder et al.,) such as HB20-3, HB20-4, HB20-25, and MB20-11; CD20 binding molecules such as the AME series of antibodies, e.g., AME 33 antibodies as set forth in WO 2004/103404 and US2005/ 0025764 (Watkins et al., Eli Lilly/Applied Molecular Evolution, AME); CD20 binding molecules such as those described in US 2005/0025764 (Watkins et al.,); A20 antibody or variants thereof such as chimeric or humanized A20 antibody (cA20, hA20, respectively) or IMMU-106 (US 2003/0219433, Immunomedics); CD20-binding antibodies, including epitope-depleted Leu-16, 1H4, or 2B8, optionally conjugated with IL-2, as in US 2005/0069545A1 and WO 2005/16969 (Carr et al.,); bispecific antibody that binds CD22 and CD20, for example, hLL2×hA20 (WO2005/ 14618, Chang et al.,); monoclonal antibodies L27, G28-2, 93-1B3, B-C1 or NU-B2 available from the International Leukocyte Typing Workshop (Valentine et al., In: *Leukocyte Typing* III (McMichael, Ed., p. 440, Oxford University Press (1987)); 1H4 (Haisma et al., *Blood* 92:184 (1998)); anti-CD20 auristatin E conjugate (Seattle Genetics); anti-CD20-IL2 (EMD/Biovation/City of Hope); anti-CD20 MAb therapy (EpiCyte); anti-CD20 antibody TRU 015 (Trubion).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). In a further embodiment, "monoclonal antibodies" can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional monoclonal antibody hybridoma techniques for isolation of monoclonal antibodies. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al., *Nature* 355:258 (1992).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Polypeptides of Immunological Interest,* 5th Ed. Public Health Service, National Institutes of Health, Bethesda, MD. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lcsk *J. Mol. Biol.* 196:901-917 (1987)). "Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.,* 151:2296 (1993); Chothia et al., *J. Mol. Biol.,* 196:901 (1987)).

Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immnol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

"Antibody fragments" comprise a portion of a full length antibody, generally the antigen binding or variable region thereof. Examples of antibody fragments include Fab, Fab', $F(ab')_2$, and Fv fragments; diabodies; linear antibodies; single-chain antibody molecules; and multispecific antibodies formed from antibody fragments. Various techniques have been developed for the production of antibody fragments. Traditionally, these fragments were derived via proteolytic digestion of intact antibodies (see, e.g., Morimoto et atl. *Journal of Biochemical and Biophysical Methods* 24:107-117 (1992) and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). In another embodiment, the $F(ab')_2$ is formed using the leucine zipper GCN4 to promote assembly of the $F(ab')_2$ molecule. According to another approach, $F(ab')_2$ fragments can be isolated directly from recombinant host cell culture. Other techniques for the production of antibody fragments will be apparent to the skilled practitioner.

In other embodiments, the antibody of choice is a single chain Fv fragment (scFv). See WO 93/16185. "Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv sec Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The expression "linear antibodies" when used throughout this application refers to the antibodies described in Zapata et al., *Polypeptide Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

"Multispecific antibodies" have binding specificities for at least two different epitopes, where the epitopes are usually from different antigens. While such molecules normally will only bind two antigens (i.e., bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g., FcγRI, or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g., $F(ab')_2$ bispecific antibodies).

Antibodies with more than two valencies are contemplated. For example, trispecific antibodies can be prepared. Tutt et al., *J. Immunol.* 147: 60 (1991).

A "naked antibody" for the purposes herein is an antibody that is not conjugated to a cytotoxic moiety or radiolabel.

An "intact antibody" herein is one which comprises two antigen binding regions, and an Fc region. Preferably, the intact antibody has a functional Fc region.

"Treatment" refers to both therapeutic treatment and prophylactic or preventative measures. Those in need of treatment include those already with the disorder as well as those in which the disorder is to be prevented.

A "disorder" is any condition that would benefit from treatment with the antibody purified as described herein. This includes both chronic and acute disorders and diseases and those pathological conditions which predispose the mammal to the disorder in question.

The phrase "ion exchange chromatography" refers to a separation technique in which compounds are separated based on their net charge. Molecules are classified as either anions (having a negative charge) or cations (having a positive charge). Some molecules (e.g., polypeptides) may have both anionic and cationic groups.

An ion-exchange resin or ion-exchange polymer is an insoluble matrix (or support structure) normally in the form of small (1-2 mm diameter) beads, fabricated from an organic polymer substrate. Horie et al. *Pure Appl. Chem.* (2004) Vol. 76, No. 4, pp. 889-906. The material has highly developed structure of pores on the surface of which are sites with easily trapped and released ions. The trapping of ions takes place only with simultaneous releasing of other ions; thus the process is called ion-exchange. There are multiple different types of ion-exchange resin which are fabricated to selectively prefer one or several different types of ions.

Most typical ion-exchange resins are based on cross linked polystyrene. The required active groups can be introduced after polymerization, or substituted monomers can be used. For example, the cross linking is often achieved by adding 0.5-25% of divinylbenzene to styrene at the polymerization process. Non-cross linked polymers are used only rarely because they are less stable. Cross linking decreases ion-exchange capacity of the resin and prolongs the time needed to accomplish the ion exchange processes. Particle size also influences the resin parameters; smaller particles have larger outer surface, but cause larger head loss in the column processes.

There are four main types of ion exchange resins differing in their functional groups: strongly acidic (typically, sulfonic acid groups, e.g. sodium polystyrene sulfonate or polyAMPS); strongly basic, (quaternary amino groups, for example, trimethylammonium groups, e.g. polyAPTAC); weakly acidic (mostly, carboxylic acid groups); weakly basic (primary, secondary, and/or ternary amino groups, e.g.

polyethylene amine). There are also specialized types: chelating resins (iminodiacetic acid, thiourea, and many others).

An ion exchange chromatography membrane will bind a compound with an overall positive or negative charge. Binding sites are located along the pores of the adsorber. The compound is transported to the binding site by convection. A positively charged membrane (anion exchanger) will bind a compound with an overall negative charge. Conversely, a negatively charged membrane (cation exchanger) will bind a compound with an overall positive charge.

Ion exchange membranes can be further categorized as either strong or weak. Strong ion exchange membranes are charged (ionized) across a wide range of pH levels. Weak ion exchange membranes are ionized within a narrow pH range. The four most common ion exchange chemistries are:

| Type of Ion Exchange | Common Abbreviation | Functional Group |
|---|---|---|
| Strong Anion | Q | Quarternary Ammonium |
| Weak Anion | D | Diethylamine |
| Strong Cation | S | Sulfonic Acid |
| Weak Cation | C | Carboxylic Acid |

In general, ion exchange membranes have pore sizes of 0.1 to 100 μm. As a reference, Sartobind Q (Sartorius AG) is a strong anion exchange membrane having a nominal pore size of 3-5 μm and is commercially available in a single or multiple layer format, and Mustang Q (Pall Corporation) is a strong anion exchange membrane having a nominal pore size of 0.8 μm and is likewise commercially available in a single or multiple layer format. As another reference, Sartobind S (Sartorius AG) is a strong cation exchange membrane having a nominal pore size of 3-5 μm and is commercially available in a single or multiple layer format, and Mustang S (Pall Corporation) is a strong cation exchange membrane having a nominal pore size of 0.8 μm and is similarly commercially available in a single or multiple layer format. As another reference, Natrix S (Natrix Separations, Inc.) is a strong cation cxchange membranc comprised of a non-woven highly fibrous durable polymeric substrate encased within a high surface area macro-porous hydrogel.

A "nominal" pore size rating describes the ability of the membrane to retain the majority of particulates at 60 to 98% the rated pore size.

The "pH" of a solution measures the acidity or alkalinity relative to the ionization of a water sample. The pH of water is neutral, i.e., 7. Most pH readings range from 0 to 14. Solutions with a higher [H+] than water (pH less than 7) are acidic; solutions with a lower [H+] than water (pH greater than 7) are basic or alkaline. pH can be measured using a pH meter. Buffer pH may be adjusted using an acid or base like HCl or NaOH.

The "pI" or "isoelectric point" of a molecule such as a polypeptide refers to the pH at which the polypeptide contains an equal number of positive and negative charges. The pI can be calculated from the net charge of the amino acid residues of the polypeptide or can be determined by isoelectric focusing. The amphoteric nature of polypeptides to have both anionic and cationic groups may be manipulated. The pH of a polypeptide may be lowered to the point where the desired polypeptide behaves as a cation (having a positive charge). Alternatively, the pH of a polypeptide may be increased to the point where the desired polypeptide behaves as an anion (having a negative charge).

The term "conductivity" refers to the ability of a solution to conduct an electric current between two electrodes. The basic unit of conductivity is the siemens (S), formerly called the mho. Conductivity is commonly expressed in units of mS/cm. Since the charge on ions in solution facilities the conductance of electrical current, the conductivity of a solution is proportional to its ion concentration. Both these measurements correlate well with the ionic strength. Ionic strength is closely related to the concentration of electrolytes and indicates how effectively the charge on a particular ion is shielded or stabilized by other ions in an electrolyte. The main difference between ionic strength and electrolyte concentration is that the former is higher if some of the ions are more highly charged. Another difference between the two is that ionic strength reflects the concentration of free ions, and not just of how much salt was added to a solution. Conductivity can be measured using a conductivity mctcr, such as various models of Orion conductivity meters. Conductivity of a solution may be altered by changing the concentration of ions therein. For example, the concentration of a buffering agent and/or the concentration of a salt (e.g., sodium chloride, sodium acetate, or potassium chloride) in the solution may be altered in order to achieve the desired conductivity. Preferably, the salt concentration of the various buffers is modified to achieve the desired conductivity.

For membrane chromatography, the "flow rate" is usually described as membrane volumes per hour (MV/h).

For membrane chromatography, the "load density" is often expressed as grams of composition processed per liter of membrane.

A "buffer" is a solution that resists changes in pH by the action of its acid-base conjugate components. Various buffers which can be cmployed depending, for example, on the desired pH of the buffer are described in *Buffers. A Guide for the Preparation and Use of Buffers in Biological Systems*, Gueffroy, D., Ed. Calbiochem Corporation (1975).

By "purifying" a polypeptide from a composition comprising the polypeptide and one or more contaminants is meant increasing the degree of purity of the polypeptide in the composition by removing (completely or partially) at least one contaminant from the composition. A "purification step" may be part of an overall purification process resulting in a "homogeneous" composition. "Homogeneous" is used herein to refer to a composition comprising at least about 70% by weight of the antibody of interest, based on total weight of the composition, preferably at least about 80% by weight, more preferably at least about 90% by weight, even more preferably at least about 95% by weight.

By "binding" a molecule to an ion exchangc membranc is meant exposing the molecule to the ion exchange membrane under appropriate conditions (pH and/or conductivity) such that the molecule is reversibly immobilized in or on the ion exchange membrane by virtue of electrostatic interactions between the molecule and a charged group or charged groups of the ion exchange membrane.

By "washing" the ion exchange membrane is meant passing an appropriate buffer through or over the ion exchange membrane.

By "eluting" a molecule (e.g., antibody or contaminant) from an ion exchange membrane is meant to remove the molecule therefrom.

For membrane chromatography, "flow-through" refers to binding of impurities to the membrane while the compound is unretained.

For membrane chromatography, "competitive adsorption" refers to more than one componcnt binding to the membrane at a given condition.

For membrane chromatography, "overload chromatography" refers to promoting competitive adsorption of both the compound of interest and impurities to the membrane. The membrane is loaded beyond the binding capacity of a compound. By exploiting the differential binding strength of the compound and impurities, wherein the impurity binds more strongly, the compound is displaced by the impurities and desorbs from the membrane and flows into the membrane effluent.

"Displacement chromatography" refers to a chromatography technique in which a sample is placed onto a column or membrane and is then displaced by a solute that is more strongly adsorbed than the components of the original mixture. The result is that the components are resolved into consecutive "rectangular" zones of highly concentrated pure substances rather than solvent-separated "peaks". Tugcu (1994) Methods in Molecular Biology: Vol 421 Affinity Chromatography: Methods and Protocols pp 71-89. Higher product concentration, higher purity, and increased throughput may be obtained compared to other modes of chromatography. Displacement chromatography is an efficient technique for the purification of proteins from complex mixtures at high column loadings in a variety of applications. Displacement chromatography is well suited for obtaining mg quantities of purified proteins from complex mixtures using standard analytical chromatography columns at the bench scale. It is also particularly well suited for enriching trace components in the feed. Displacement chromatography can be readily carried out using a variety of resin systems including, ion exchange, HIC and RPLC. Freitag and Breier. (1995) *J. Chromatogr. A* 691, 101-112.

The phrase "mixed mode" refers to a sorbent that has the ability to separate compounds based on two different mechanisms, e.g. a separation based on hydrophilicity/hydrophobicity differences between polypeptides overlaid on a separation based on net charge. This is often accomplished by using a multi-modal ligand that may interact with a target molecule in several different ways including ionic interaction and hydrogen bonding or hydrophobic interaction. Sorbents like GE Healthcare Capto™ MMC and Capto™ Adhere are examples of "mixed mode" chromatography resins.

A "depth filter" is a variety of filter that uses a porous filtration medium to retain particles throughout the medium, rather just on the surface of the medium. These filters are commonly used when the fluid to be filtered contains a high load of particles because, relative to other types of filters, they can retain a large mass of particles before becoming clogged.

A "monolith" refers to a chromatographic media comprised of a porous substrate that has been chemically altered for a specific application. Ion exchange monoliths have been developed as an alternative to chromatographic resin, typically demonstrating high permeability and short diffusion distances resulting in better mass transport and lower pressures, enabling their use at higher flow rates and/or shorter residence times.

MODES FOR CARRYING OUT THE INVENTION

The invention herein provides methods for purifying a polypeptide from a composition (e.g., an aqueous solution) comprising the polypeptide and one or more contaminants. The composition is generally one resulting from the recombinant production of the polypeptide, but may be that resulting from production of the polypeptide by peptide synthesis (or other synthetic means) or the polypeptide may be purified from a native source of the polypeptide. Preferably the polypeptide is a $C_H2/C_H3$ region-containing polypeptide. In preferred embodiments, the $C_H2/C_H3$ region-containing polypeptide is an antibody.

Recombinant Production of Antibodies

For recombinant production of the polypeptide, the nucleic acid encoding the polypeptide sequence is isolated and inserted into a replicable vector for further cloning (amplification of the DNA) or for expression. DNA encoding the polypeptide is readily isolated and sequenced using conventional procedures (e.g., by using oligonucleotide probes that are capable of binding specifically to genes encoding the heavy and light chains of an antibody). Many vectors are available. The vector components generally include, but are not limited to, one or more of the following: a signal sequence, an origin of replication, one or more marker genes, an enhancer element, a promoter, and a transcription termination sequence (e.g., as described in U.S. Pat. No. 5,534,615, specifically incorporated herein by reference).

Suitable host cells for cloning or expressing the DNA in the vectors herein are prokaryote, yeast, or higher eukaryotic cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045). *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of Spodopterafrugiperda cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines include, but are not limited to, monkey kidney CV1 cells transformed by SV40 (COS-7, ATCC CRL 1651); human embryonic kidney cells (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N. Y. Acad. Sci.* 383:44-68 (1982)); MRC 5 cells; FS4 cells; and human hepatoma cells (Hep G2). Often, CHO cells are preferred for the expression of antibodies, and may be advantageously used to produce the antibodies purified in accordance with the present invention.

Host cells are transformed with the above-described expression or cloning vectors for polypeptide production and cultured in conventional nutrient media modified as appropriate for inducing promoters, selecting transformants, or amplifying the genes encoding the desired sequences.

The host cells used to produce the polypcptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), aminoglycoside antibiotics (such as gentamicin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the polypeptide can be produced intracellularly, in the periplasmic space, or directly secreted into the medium. If the polypeptide is produced intracellularly, as a first step, the particulate debris, either host cells or lysed cells (e.g., resulting from homogenization), is removed, for example, by centrifugation or ultrafiltration. Where the polypeptide is secreted into the medium, supernatants from such expression systems may be concentrated using a commercially available protein concentration filter, for example, an Amicon or Millipore Pellicon ultrafiltration unit.

One aspect of the present invention considers the impact of gentamicin on CEX columns. Gentamicin, and other aminoglycoside antibiotics, can be used as a bactericidal additive in the cell culture applications to prevent non-resistant contaminations. When added to a cell culture it must be removed as a process related impurity. Typical removal is accomplished using an affinity chromatography step, however, in some processes an affinity step may not be the first purification step.

As a cationic aminoglycoside antibiotic, gentamicin is positively charged at or below neutral pH. If a CEX column were the first chromatography step, with the intention of binding the polypeptide of interest at or below neutral pH, gentamicin would be competing for binding sites on the column. Previous work has demonstrated that gentamicin will bind stronger than an antibody to a CEX membrane or rcsin, The effect on a CEX column is an apparent decrease in antibody binding capacity.

Another aspect of the present invention considers the impact of polyethyleneimine (PEI), or other cationic polymers, on CEX columns. PEI can be used as a pre-harvest flocculation agent in an *E. coli* polypeptide purification processes. When PEI is added after a cell homogenization step, it acts as an impurity binder and makes both centrifugation and filtration more robust processes. A concern with incorporating this step is the effect of any extra PEI that isn't used to flocculate impurities because it then remains in the purification pools that eventually come in contact with the CEX columns.

There are many different forms of PET, ranging from linear or branched polymers, and they can contain primary, secondary, or tertiary amines. The shape of the PET isn't as much of a concern as the fact that it is positively charged at the majority of processing conditions. Therefore it will bind to a CEX column very strongly. Furthermore, the first chromatography step for most *E. coli* proteins may be a CEX column due to their relatively high binding capacities. Additionally, due to the strong binding of the CEX column to PEI, it occasionally requires the use of a weaker CEX column so that the PEI can be eluted from the column after each run.

Previous work has demonstrated that when varying levels of PEI are used for flocculation, the binding capacity of the CEX column will increase as lower PEI levels are used. It has also been observed that the CEX chromatography step yield will increase with lower levels of PEI in the load.

Using a similarly charged ion exchange membrane prior to an ion exchange column to decrease impurities can result in increases in binding capacity, yield, impurity clearance, all of which can enable a more efficient process and reduced operating costs.

The Membrane Ion Exchange Chromatography Method of the Invention

In the preferred embodiment of the invention, the composition to be subjected to the purification method herein is a recombinantly produced polypeptide, preferably an intact antibody, expressed by a Chinese Hamster Ovary (CHO) or *E. coli* recombinant host cell culture. Optionally, the composition has been subjected to at least one purification step prior to membrane ion exchange chromatography. The composition contains the polypeptidc of interest and one or more contaminants, such as Chinese Hamster Ovary Proteins (CHOP); *E. coli* Proteins (ECP); leached protein A; nucleic acid; a variant, fragment, aggregate or derivative of the desired antibody; another polypeptide; endotoxin; viral contaminant; aminoglycoside antibiotic components (e.g., gentamicin); or an ionic polymer added to the purification process (e.g., polyethyleneimine (PEI), polyvinylamine, polyarginine, polyvinylsulfonic acid, polyacrylic acid), etc.

Examples of additional purification procedures which may be performed prior to, during, or following the membrane ion exchange chromatography method include fractionation on a hydrophobic interaction chromatography (e.g., on PHENYL-SEPHAROSE™), ethanol precipitation, thermal precipitation, polyethylene glycol (PEG) precipitation, isoelectric focusing, Reverse Phase HPLC, chromatography on silica, chromatography on HEPARIN SEPHAROSE™, anion exchange chromatography, cation exchange chromatography, mixed mode ion exchange, chromatofocusing, SDS-PAGE, ammonium sulfate precipitation, hydroxyapatite chromatography, gel electrophoresis, dialysis, hydrophic charge induction chromatography, high performance tangential flow filtration (HPTFF), and affinity chromatography (e.g., using protein A, protein G, an antibody, or a specific substrate, ligand or antigen as the capture reagent).

When using recombinant techniques, the polypeptide can be produced intracellularly, in the periplasmic space, or directly secreted into the medium. If the polypeptide is produced intracellularly, as a first step, the particulate debris, either host cells or lysed fragments, is removed, for example, by centrifugation or filtration. Where the polypeptide is secreted into the medium, the recombinant host cells may be separated from the cell culture medium by centrifugation or filtration, for example.

In the case of isolating antibodies, the majority of the purification occurs during protein A affinity chromatography, if used as the first step. Protein A is a bacterial cell wall protein that binds specifically to the Fc region of antibodies. When immobilized onto chromatography media, protein A provides a technique for purifying recombinant antibodies because it can selectively bind antibodies in complex solutions, allowing impurities to flow through.

The basic protocol of protein A affinity column is straightforward: bind at about neutral pH and elute at acid pH. Protein A immobilized on a solid phase is used to purify the $C_H2/C_H3$ region-containing polypeptide. The solid phase is preferably a column comprising a glass, silica, agarose, or polystyrenedivinylbenzene surface for immobilizing the protein A. Preferably, the solid phase is a controlled pore glass column, silicic acid column, or highly cross-linked agarose column. A Mabselect SuRe™ column, commercially available from GE Healthcare, is an example of a highly cross-linked agarose protein A column effective at purifying antibodies. Sometimes, the column has been coated with a reagent, such as glycerol, in an attempt to prevent nonspecific adherence to the column. The PROSEP A™ column, commercially available from Millipore Corporation, is an example of a protein A controlled pore glass column which is coated with glycerol. The solid phase for the protein A chromatography is equilibrated with a suitable buffer.

The contaminated preparation derived from the recombinant host cells is loaded on the equilibrated solid phase using a loading buffer which may be the same as the equilibration buffer. As the contaminated preparation flows through the solid phase, the polypeptide is adsorbed to the immobilized protein A, and other contaminants (such as Chinese Hamster Ovary Proteins, CHOP, where the polypeptidc is produced in a CHO cell, gentamicin, and polyethyleneimine (PEI)) bind nonspecifically to the solid phase.

The next step performed sequentially entails removing the contaminants bound to the solid phase by washing the solid phase with a solution containing a salt, amino acid, and/or hydrophobic electrolyte solvent in an intermediate wash step. In preferred embodiments, the salt in this wash is potassium phosphate, the amino acid is arginine, and the hydrophobic electrolyte is TEMAC and/or TEAC. While a single solute may be present in the wash, in certain embodiments, two or more such solutes may be used. The solute(s) are preferably added to a pH buffered solution having a pH at about neutrality.

Following the intermediate wash step of the preceding paragraph, the polypeptide of interest is recovered from the column. This is normally achieved using a suitable elution buffer. The polypeptide may, for example, be eluted from the column using an elution buffer having a low pH, e.g., in the range from about 2 to about 5, and preferably in the range from about 2.5 to about 3.5. Examples of elution buffers for this purpose include citrate or acetate buffers.

Membrane ion exchange chromatography is performed as claimed herein. A decision is first made as to whether an anion or cation exchange membrane is to be employed. Although the isoelectric point (pI) of some antibodies ranges from approximately 6.7 to 9.4, the p1 of many antibodies is high (often >8 and sometimes >9). In general, a cation exchange membrane may be used for antibodies with pI's greater than about 8, and an anion exchange membrane may be used for antibodies with pI's less than about 8.

For membrane cation exchange chromatography run in overload mode, the pH of the load material is adjusted to about 1 to about 5 pH units below the pI of the antibody, the conductivity of the load material is adjusted to ≤ about 40 mS/cm, depending on the pH, and the antibody is then pumped through the membrane. In some embodiments, the pH of the load material is adjusted to about 1 to about 4 pH units, about 1 to about 3 pH units, about 1 to about 2 pH units, or about 1 pH unit, below the pI of the antibody. In other embodiments, the conductivity of the load material is adjusted to ≤ about 20 mS/cm or ≤ about 10 mS/cm, depending on the pH. Because the pH of the load is less than the pI of the antibody, the antibody (which has become positively charged) will NOT flow through initially. Rather, the antibody will be electrostatically bound to the negative functional groups of the cation exchanger. This is because the antibody (positive) and membrane (negative) have opposite charge. Since the pI of many contaminants, e.g., host cell proteins, such as CHOP or ECP, aminoglycoside antibiotics, such as gentamicin, and ionic polymer additives, such as polyethyleneimine (PEI), that elute with the antibody during protein A affinity chromatography is only slightly different from the pI of the antibody, that is, the pIs may differ by only about 0.05 to about 0.2 pI units, these contaminants, like the "basic" antibodies, will also bind to the membrane. In purification schemes where Protein A chromatography is not used, gentamicin or PEI or other impurities will remain in high enough concentrations to disrupt the performance of an IEX column unless a membrane is used. Without being bound by theory, it appears that for membrane cation exchange chromatography run in overload mode, at pH and conductivity conditions that induce charge with minimal ionic shielding, competitive adsorption occurs and the contaminants preferentially bind to the membrane, or otherwise effectively "displace" the antibody from the membrane (R R Drager, F E Regnier, J Chromatogr. 359:147-55 (1986)), allowing the antibody to "elute" from the matrix or flow through after binding and be recovered in the effluent.

For membrane anion exchange chromatography run in overload mode, the pH of the load material is adjusted to about 1 to about 5 pH units above the pI of the antibody, the conductivity of the load material is adjusted to ≤ about 40 mS/cm, depending on the pH, and the antibody is then pumped through the membrane. In some embodiments, the pH of the load material is adjusted to about 1 to about 4 pH units, about 1 to about 3 pH units, about 1 to about 2 pH units, or about 1 pH unit, above the pI of the antibody. In other embodiments, the conductivity of the load material is adjusted to ≤ about 20 mS/cm or ≤ about 10 mS/cm, depending on the pH. Because the pH of the load is greater than the pI of the antibody, the antibody (which has become negatively charged) will NOT flow through initially. Rather, the antibody will be electrostatically bound to the positive functional groups of the anion exchanger. This is because the antibody (negative) and membrane (positive) have opposite charge. Since the pI of many contaminants, e.g., host cell proteins, such as CHOP, that elute with the antibody during protein A affinity chromatography is only slightly different from the pI of the antibody, that is, the pIs may differ by only about 0.05 to about 0.2 pI units, these contaminants, like the "acidic" antibodies, will also bind to the membrane. Without being bound by theory, it appears that for membrane anion exchange chromatography run in overload mode, at pH and conductivity conditions that induce charge with minimal ionic shielding, competitive adsorption occurs and the contaminants preferentially bind to the membrane, or otherwise effectively "displace" the antibody from the membrane (R R Drager, F E Regnier, *J Chromatogr.* 359:147-55 (1986)), allowing the antibody to "elute" from the matrix or flow through after binding and be recovered in the effluent.

In one example, membrane chromatography is run on either a standard chromatography system or a custom chromatography system like an AKTA™ Explorer (GE Healthcare) equipped with pressure gauges, sensors, and pump plus pump controllers. In this example, the membrane device is installed downstream of a pressure gauge. In said example, the pH and conductivity detectors are installed downstream of the membrane device. Continuing with this example, the system is thoroughly flushed with water and then with equilibration buffer before the installation of the membrane. Continuing further with the example, the system with the membrane is flushed with equilibration buffer until the solution pH and conductivity outlet match the equilibration buffer specification (about five membrane volumes) and a stable baseline is observed. Continuing even further with this example, the feed material is loaded by a pump at 333-2667 MV/hour, pH 5.5 (for purification of a hypothetical "basic" antibody) or pH 8.0 (for purification of a hypothetical "acidic" antibody), and a conductivity of approximately 4 mS/cm. Continuing still further with this example, the operation backpressure, and pH and conductivity changes during the operation are recorded. Finally, in this example, the polypeptidc in the membrane effluent is collected immediately when an ultraviolet (UV) absorbance trace at 280 nm is 0.2 absorbance units over the baseline. After loading the feed material, the membrane is washed with an appropriate wash buffer, and the pool collection is stopped once the UV trace at 280 nm is below 0.2 absorbance units, and the samples from the pool in the membrane effluent fraction are assayed for polypeptide concentration, dimer/aggregation level, host cell proteins, DNA, and leached protein A. The step recovery is typically calculated using the polypeptide loaded and the polypeptide in the membrane effluent. The membrane is traditionally one-time-use only. Regarding analytical assays, polypeptide content (polypcptide concentration) may be determined by absorbance at 280 nm using a Beckman spectrophotometer. Polypeptide aggregation may be determined by size-exclusion chromatography. Host cell protein, e.g., CHOP or ECP, levels may be analyzed by an enzyme-linked immunosorbent assay (ELISA). Host-cell DNA may be quantitated by employment of TaqMAN PCR (polymerase chain reaction). Leached protein A may be performed using the immunochemical ELISA-based method recommended by the protein A resin vendor. Gentamicin may be analyzed by ELISA and polyethyleneimine (PEI), levels may be quantitated by Q Sepharose Fast Flow chromatography or nuclear magnetic resonance (NMR).

The following buffers are hypothetically designed and tested for use with the S membrane: (1) 89 mM acetic acid, 127 mM TRIS base, 21 mM citric acid, pH 5.5, 6.0 mS/cm, (2) 28 mM MES, 95 mM NaCl, pH 6.0, 11 mS/cm, (3) 200 mM NaOAc, pH 5.5, 12 mS/cm, (4) 100 mM NaOAc, pH 5.5, 6.4 mS/cm, (5) 96 mM acetic acid, 65 mM TRIS, pH 5.0, 3.6 mS/cm, (6) 25 mM MOPS, pH 7.1, 0.8 mS/cm, (7) 50 mM HEPES, 90 mM NaCl, pH 7.0, 10 mS/cm, (8) 0.5× phosphate buffered saline (PBS), 4.5 mM acetic acid, pH 5.0, 8.0 mS/cm, 25 mM NaOAc, pH 5.0, 6.0 mS/cm.

The following buffers are hypothetically designed and tested for use with the Q membrane: (1) 50 mM TRIS, 15 mM NaCl, pH 8.0, 4.3 mS/cm, (2) 25 mM TRIS, pH 8.0, 1.3 mS/cm, (3) 60 mM TRIS, 118 mM NaCl, pH 8.0, 15.7 mS/cm, (4) 50 mM TRIS, 50 mM NaOAc, pH 8.0, 7.0 mS/cm, (5) 25 mM HEPES, 85 mM NaOAc, pH 7.0, 6.5 mS/cm, and (6) 91 mM acetic acid, 130 mM TRIS, pH 8.0, 5.0 mS/cm, (7) 75 mM glycine, 9 mM phosphoric acid, 115 mM TRIS, pH 8.9, 0.8 mS/cm (8) 25 mM TRIS, 5 mM NaCl, pH 8.9, 1.0 mS/cm. (9) 25 mM TRIS, 10 mM NaCl, pH 9.0, 1.5 mS/cm, (10) 1x phosphate buffered saline (PBS), pH 7.3, 15.2 mS/cm Additionally, any buffer system can be pH adjusted up or down with the addition of acetic acid, citric acid, HEPES, hydrochloric acid, phosphoric acid, sodium hydroxide, TRIS, or other such acidic and basic buffers to reach a suitable pH. Any buffer system can also be conductivity adjusted up or down using purified water, water for injection (WFI), sodium acetate, sodium chloride, potassium phosphate, or other such low and high salt containing buffers to reach a suitable conductivity.

Development of the competitive adsorption membrane chromatography step involves running the load material through the membrane at various levels of pH and conductivity. The retention of the polypeptide, either polypeptide of interest or contaminant, can be enhanced when the molecule has a large electrostatic interaction. Electrostatic interactions can be enhanced when operating under conditions where the polypeptides are highly charged, i.e., when using a buffer having a pH sufficiently distinct from the pI of the polypeptide, enhancing the charge of the polypeptide, and a low ionic strength to prevent the shielding of charges by buffer ions. In contrast, electrostatic interactions can be reduced when operating under conditions where the polypeptides are poorly charged, i.e., when using a buffer having a pH sufficiently close to the pI of the polypeptide, reducing the charge of the polypeptide, and a high ionic strength to permit the shielding of charges by buffer ions. As a result, polypeptides having different physico-chemical properties can be separated by membrane adsorption by optimizing buffer solution. Some molecules can be retained on a given membrane while other ones flow through based on the appropriate selection of the pH and ionic strength of the buffer.

The polypeptide preparation obtained according to the membrane ion exchange chromatography method herein may be subjected to additional purification steps, if necessary. Exemplary further purification steps have been discussed above.

Referring to FIG. 1, one example of a successful purification scheme for an antibody is a recovery process entailing an initial capture step of protein A affinity chromatography, followed by a cation exchange column in run in bind and elute mode, followed by a final polishing step or steps.

Referring to FIG. 1, one example of an improved purification scheme is a recovery process entailing an initial capture step of protein A affinity chromatography, followed by a cation exchange membrane run in overload mode protecting a cation exchange column run in bind and elute mode, followed by a final polishing step or steps.

Referring to FIG. 1, another example of an improved purification scheme is a recovcry process entailing an initial cation exchange membrane run in overload mode protecting a cation exchange column run in bind and elute mode, followed by a polishing step or steps.

Referring to FIG. 2, one example of a successful purification scheme for a non-antibody is a recovery process entailing an initial capture step of cation exchange chromatography, followed by a final polishing step or steps.

Referring to FIG. 2, one example of an improved purification scheme is a recovery process entailing an initial cation exchange membrane run in overload mode protecting a cation exchange column run in bind and elute mode, followed by a polishing step or steps.

Unlike applications that use the IEX membranes primarily as a sole purification step or final polishing step, the membranes in the present purification method are being used to protect a similarly charged ion exchange membrane (e.g. a cation exchange membrane placed directly in front of a cation exchange resin). This is beneficial because the membranes are more selective for impurities than polypeptides/antibodies so they reduce or eliminate the impurities going onto the column. The impurities can also displace the polypeptide/antibody so that it eventually makes its way onto the column. The membranes can be used either continuously or non-continuously with the aforementioned column.

Using the membranes prior to the similarly charged ion exchange column in this purification method may be advantageous whenever impurities in the load are decreasing the performance of the cation exchange column. By removing those impurities with the membrane, it may allow the cation exchange column to be loaded to higher binding capacity, resulting in a reduced column size or a decreased number of cycles per run. Alternatively, by removing those impurities with a membrane, it may allow the cation exchange column to have an increase step yield, or have a longer resin lifetime before being discarded, or result in decreased impurity levels in the cation exchange pool, or decrease the number of downstream polishing steps. It may also allow a cation exchange column to replace a protein A affinity column which may be advantageous if a cheaper alternative to protein A affinity resin were needed, or if the polypeptide of interest will not bind to a protein A affinity resin. Using a cation exchange membrane and cation exchange column in continuous operation may be advantageous by reducing total processing time, buffers, or equipment such as tanks or chromatography skids.

Optionally, the polypeptide is conjugated to one or more heterologous molecules as desired. The heterologous molecule may, for example, be one which increases the serum half-life of the polypeptide (e.g., polyethylene glycol, PEG), or it may be a label (e.g., an enzyme, fluorescent label and/or radionuclide), or a cytotoxic molecule (e.g., a toxin, chemotherapeutic drug, or radioactive isotope etc).

A therapeutic formulation comprising the polypeptide, optionally conjugated with a heterologous molecule, may be prepared by mixing the polypeptide having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. "Pharmaceutically acceptable" carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-crcsol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dcxtrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The active ingredients may also be entrapped in microcapsule prepared, for example, by coaccrvation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulation to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The polypeptide purified as disclosed herein or the composition comprising the polypeptide and a pharmaceutically acceptable carrier is then used for various diagnostic, therapeutic or other uses known for such polypeptides and compositions. For example, the polypeptide may be used to treat a disorder in a mammal by administering a therapeutically effective amount of the polypeptide to the mammal.

The following example(s) are offered by way of illustration and not by way of limitation. The disclosures of all citations in the specification are expressly incorporated herein by reference.

EXAMPLES

Example 1

Introduction

This study focuses on the purification of monoclonal antibodies using ion exchange membranes in competitive adsorption mode to enhance the efficiency of downstream columns. Since membranes operating in competitive adsorption mode bind many impurities more strongly than monoclonal antibodies or other polypeptides of interest, the membrane effectively removes impurities that can have a detrimental effect on a similarly charged, downstream column.

This approach is counter-intuitive to many purification processes which try to eliminate redundant cation exchange or anion exchange purification steps. In this application, a redundant membrane prior to a downstream column can enhance the performance of the column such that the overall process is more efficient.

One recombinant DNA derived mAb, one recombinant DNA derived one-armed antibody, and one recombinant DNA derived polypeptide were selected for analysis based on their molecular variety. The mAb was produced in CHO cell cultures and varied in degrees of purification ranging from no chromatography purification to three column chromatography steps (Protein A, anion exchange, and cation exchange). The one-armed antibody was produced in *E. coli* cell cultures and had been purified through a Protein A chromatography step. The polypeptide was produced in *E. coli* cell cultures and had no prior chromatography purification. Feedstreams were chosen based on residual levels of impurities that could negatively affect a chromatography column.

This study explores the ability for impurities, such as gentamicin and polyethyleneimine (PEI), to negatively affect ion exchange columns and the ability of ion exchange membranes, such as Mustang™ S and Natrix S, to clear those impurities resulting in improved column performance.

Materials and Methods

Feedstream

The feedstreams were taken from industrial, pilot, or small-scale cell culture batches (Genentech Inc., South San Francisco, Califfornia) initially produced for commercial or research purposes. Feedstreams had varying degrees of purification, meaning the cells were separated and the clarified fluid was or was not purified over at least one column chromatography step. Each feedstream contained a target therapeutic polypeptide and a quantifiable level of impurities. The composition of each feedstream varied depending on the individual polypeptide process and the level of purification. Table 1 shows feedstream characteristics for each of the antibodies, polypeptides, or monovalent antibodies used in this study.

TABLE 1

Feedstream characteristics.

| Product[a] | Molecule Type | Upstream Process | Nomenclature | pH | Cond. (mS/cm) | Conc. (g/L) | IgG type | Molecular Weight (kDa) | pI[c] |
|---|---|---|---|---|---|---|---|---|---|
| mAb 1 | Monoclonal antibody | Protein A, Anion Exchange Flow-Through | Anion Exchange Pool | 8.0 | 5.0 | 5.4 | 1 | 144 | 9.3 |
| mAb 2 | Monoclonal antibody | Protein A, Cation Exchange Bind/Elute | Cation Exchange Pool | 5.5 | 9.0 | 4.1 | 1 | 145 | 7.7 |
| mAb 3 | Monoclonal antibody | Centrifugation | Centrate (HCCF) | 7.6 | 10.5 | 1.2-1.4 | 1 | 149 | 8.9 |
| | | Protein A[b] | Protein A Pool | 5.5 | 3.2 | 5.9-6.9 | | | |
| | | Protein A, Anion Exchange Flow-Through[b] | Anion Exchange Pool | 5.5 | 6.0 | 4.8 | | | |
| | | Protein A, Anion Exchange, Cation Exchange, UF/DF | UF/DF Pool | 6.2 | 4.2 | 31.6 | | | |
| Monovalent Antibody 1 | Monovalent antibody | Extraction, PEI Conditioning, Centrifugation, Protein A | Protein A Pool | 6.7 | 2.5 | 4.7 | N/A | 97 | 8.3 |
| Polypeptide 1 | Polypeptide | Extraction, PEI Conditioning, Centrifugation | Centrate | 7.0 | 8.0 | 6.6-7.5 | N/A | 60 | 9.1 |

[a]Feedstock samples for all products were collected from industrial, pilot, and small-scale processes.
[b]Pool pH and conductivity have been previously adjusted to ensure adequate product stability.
[c]The isoelectric point (pI) was calculated based on the amino acid sequence for each mAb.

Polypeptide Quantification

The concentration of polypeptide was determined using three methods. When impurity levels were too low to have an appreciable effect on UV absorbance, a UV-spectrophotometric scan at 280 and 320 nm was used. When impurity levels or color may have had an appreciable effect on UV absorbance, an analytical affinity column or ion exchange column was used to quantify antibody or polypeptide concentrations, respectively.

For samples tested by UV-spectrophotometric scan, the samples containing polypeptide were diluted with appropriate non-interfering diluent into the range of 0.1 to 1.0 AU. Sample preparation and spec scan readings were performed in duplicate and the average value was recorded. The absorption coefficient for the polypeptides tested was 1.45-1.70 $(mg/mL)^{-1}cm^{-1}$. The absorbance at 280 and 320 nm, dilution factor, path length (1 cm), and absorption extinction coefficient were used to calculate the mAb concentration using the equation known as the Beer-Lambert Law.

$$\text{Protein Concentration (mg/mL)} = \frac{A_{280} - A_{320}}{\text{abs. } coeff.} \times \text{dilution factor}$$

For samples tested by analytical affinity columns, the samples containing antibody were diluted with appropriate non-interfering diluent, if needed, into the range of 0.025-4.0 mg/mL. Alternatively, the injection volume could be doubled or halved for lower or higher concentration samples, respectively. Sample preparation and HPLC testing were performed in duplicate and the average value was recorded. As a generic antibody HPLC assay, the sample concentration results are corrected for the specific antibody by using the corresponding absorption extinction coefficient against the reference material's antibody absorption extinction coefficient.

For samples tested by analytical ion exchange column, the samples containing polypeptide were diluted with appropriate non-interfering diluent, if needed, into the range of 0.1-0.8 mg/mL. Sample preparation and HPLC testing were performed in duplicate and the average value was recorded. The sample concentration results arc determined by integrating the area under the injection peak and correlated to a standard curve using reference material.

CHO Host Cell Proteins (CHOP) Quantification

An enzyme linked immunosorbent assay (ELISA) was used to quantitate the levels of CHOP. Affinity-purified goat anti-CHOP antibodies were immobilized on microtiter plate wells. Dilutions of the samples containing CHOP, standards, and controls, were incubated in the wells, followed by incubation with goat anti-CHOP antibodies conjugated to horseradish peroxidase. The horseradish peroxidase enzymatic activity was detected with o-phenylenediamine dihydrochloride. The CHOP was quantitated by reading absorbance at 492 nm in a microtiter plate reader. A computer curve-fitting program was used to generate the standard curve and automatically calculate the sample concentration. The assay range for the ELISA was typically 5 ng/ml to 320 ng/ml. For each sample, 2-4 dilutions were assayed and the values were averaged. CHOP values were divided by the protein concentration and the results were reported in units of ppm (ng CHOP/mg protein).

*E. Coli* Proteins (ECP) Quantification

An enzyme linked immunosorbent assay (ELISA) was used to quantitate the levels of ECP in a similar manner as for CHOP Quantification.

Gentamicin Quantification

An enzyme linked immunosorbent assay (ELISA) was used to quantitate the levels of gentamicin. Goat polyclonal antibody to gentamicin-BSA is immobilized on microtiter plate wells. Gentamicin competes with biotin-gentamicin for binding to the antibody. The amount of bound biotin-gentamicin is measured with horseradish peroxidase-streptavidin whose enzymatic activity is detected with tetramethyl benzidine (TMB). Samples are diluted with the ELISA assay diluent according to the acceptable dilution established during sample qualification. The gentamicin is quantitated by reading absorbance at 450 nm in a microtiter plate reader. A minimum 4-parameter computer curve-fitting program is used to generate the standard curve and automatically calculate the sample concentration. Typically, the reporting range for the standard curve in the gentamicin assay is 0.58 ng/mL to 90 ng/mL. For each sample, 2-4 dilutions were assayed and the values were averaged. Gentamicin values were divided by the protein concentration and the results were reported in units of ppm (ng gentamicin/mg protein).

Polyethyleneimine Quantification

All data was recorded on a Bruker 600 MHz spectrometer equipped with a 5 mm gradient-equipped TCI cryoprobe and an auto sampler. Data was acquired using a spin-echo pulse sequence designed to minimize resonance signals from the protein in solution. An excitation sculpting pulse sequence coupled with a presaturation pulse sequence was designed to minimize the resonance signal from water in solution. Prior to the NMR measurement, $D_2O$ was added to all samples to a final concentration of 10% (630 mL of sample+70 mL of $D_2O$).

The quantitative NMR assay is a general analytical method and can be applied to an exceptionally large number of organic molecules. Generally, every molecule has a unique set of NMR signals with characteristic resonance frequencies, relative peak intensities, line widths, and coupling patterns. The only criteria for the NMR assay to be suitable for determining concentration of a small, proton-containing molecule is that the NMR signal of analyte and the buffer components do not overlap. The NMR assay is accurate and precise over a large range of analyte concentrations (for example, 1 ug/mL to 154,500 ug/mL for propylene glycol.)

Chromatography Membranes

The membranes tested were the Mustang™ S (Pall Corporation, East Hills, N.Y.) and Natrix S (Natrix Separations, Burlington, Canada). The Mustang™ S and Natrix S are strong cation exchange membranes that effectively bind positively-charged proteins and viral particles. The Mustang™ S is made of polyethersulfone (PES) with 0.8 μm pores and modified with a form of sulfonic acid. The Natrix S membrane consists of a polymeric hydrogel formed within a flexible porous support matrix. The support matrix provides mechanical strength, while the hydrogel properties determine the separation chemistry of the product. To increase binding capacity the manufacturer can combine multiple layers of membrane into each device. The total number of layers and thickness vary depending on the manufacturer and the size of the device being fabricated. Membrane volume (MV) is the physical volume of the membrane (solids and voids) and is measured in units of mL. A variety of membrane devices representing multiple scales were used in this study. Table 2 lists the pertinent specifications for each membrane tested.

TABLE 2

| Strong cation exchange membrane characteristics. | | | | | | |
|---|---|---|---|---|---|---|
| Membrane | Manufacturer | Device | Part No. | Layers No. | Membrane Volume (MV) mL | Pore Size μm |
| Mustang ™ S | Pall Corporation | 25 mm Acrodisc ® | MSTG25S6 | 6 | 0.18 | 0.8 |
| Mustang ™ Q | | Coin | MSTG18Q16 | 16 | 0.35 | 0.8 |
| Natrix S | Natrix Separations, Inc. | 25 mm Syringe Column | NX1001 | 1 | 0.23 | N/A |
| | | 50 mm Syringe Column | NX1101 | 1 | 0.75 | N/A |

Chromatography Resins

The resins tested were the Fractogel SE Hicap (EMD Chemicals Inc., Gibbstown, New Jersey) and SP Sepharose Fast Flow (GE Healthcare Life Sciences, Piscataway, New Jersey). The Fractogel SE Hicap and SP Sepharose Fast Flow resins are strong cation exchange resins. The Fractogel SE Hicap resin is made of cross linked polymethacrylate particles of 40-90 μm diameter with pore size of about 800 Å. The functional ligand is covalently attached to the particle with a long, linear polymer chain. The SP Sepharose Fast Flow resin is made of highly cross-linked agarose particles of 45-165 μm diameter with a ~4,000,000 Da exclusion limit. Sepharose Fast Flow is a cross-linked derivative of Sepharose with a sulfopropyl ligand as the functional group. The cross-linking method is proprietary to the manufacturer.

Membrane and Resin Purification Systems

Small-scale tests were performed with an AKTA Explorer™ 100 (GE Healthcare, Fairfield, Connecticut), which is a programmable process purification system that includes an integrated metering pump, pressure sensor, and in-line pH, conductivity, and UV sensor. The Explorer system was programmed and controlled through a computer running UNICORN™ v5.10 software (GE Healthcare, Fairfield, Connecticut). Small-scale tests were also performed using a manual system consisting of a Masterflex® US® digital economy drive peristaltic pump (Cole Parmer, Vernon Hills, Illinois), in-line DTX™ Plus TNF-R pressure sensor (Becton Dickinson, Franklin Lakes, New Jersey), and a AND EK-1200i balance (A&D Company, Ltd., Tokyo, Japan). The balance was used to physically monitor the flow rate of the pump by measuring mass accumulation. Mass was converted to volume assuming a feedstream density of 1.0 g/mL. The pressure from the in-line transducers and mass from the balance were continuously monitored using a NetDAQ™ 2640A/41A network data acquisition system (Fluke, Everett, Washington) which was linked to a computer running Trendlink™ version 3.1.1 (Canary Labs Inc., Martinsburg, Pennsylvania) and RsCom version 2.40 (A&D Company, Ltd., Tokyo, Japan) software for pressure and mass collection, respectively.

Membrane Flow Through Sample Collection Techniques

Flow through samples were collected in three different ways. Grab samples and fractions were the most common. A grab sample is a small instantaneous aliquot of flow through taken at a specific throughput. Fractions are larger flow through samples and are defined by throughput ranges. Flow through was also collected as a single large pool. Pool analysis is effective, but grab samples and fractions are generally more useful for monitoring mAb and impurity levels because consecutive samples can be combined to show trends.

Dynamic Binding Capacity (DBC) Techniques

The dynamic binding capacities (DBC) of membranes and resins were determined by loading the feedstream onto the media at a typical process flow rate. This was preferred rather than letting the media soak in the load feedstream, as typically done to determine a static binding capacity. For this application, the DBC was a more appropriate measure of the medias' performance. The DBC was determined by taking flow through grab samples or fractions during the loading phase. Using the specific throughput for grab samples or the volume of all fractions and the concentration of the polypeptide or impurity for all grab samples or fractions enabled a DBC graph to be generated. Additionally, if the polypeptide or impurity concentrations in the load material was known, a graph could be generated to compare the filtrate concentrations (C) to the load concentration ($C_0$). In this case, a $C/C_0$ value of 0 indicates the filtrate concentration is much lower than the load concentration, while a $C/C_0$ value of 1 indicates the filtrate concentration is similar to the load concentration.

Experimental

Feedstock was removed from cold storage (2-8° C. or ≤−70° C.) and allowed to equilibrate to room temperature. It was then optionally pH and/or conductivity adjusted from the conditions shown in Table 1 using appropriate titrating agent (i.e. 1.5 M tris base or 1 M citric acid) or diluent (purified water or 5 M sodium chloride). It was then filtered offline using an AcroPak™ 20 (Pall Corporation, East Hills, New York), AcroPak™ 1000 (Pall Corporation, East Hills, New York), or 1000 mL vacuum filter (Thermo Fisher Scientific, Rochester, New York) to remove any precipitates that may have formed during cold storage or conditioning.

The purification system was prepared by flushing the load and flow through lines using purified water or appropriate buffer. The membrane was placed in-line downstream of the feed pump and pressure sensor and then it was flushed with 50-500 MV of purified water or equilibration buffer. After flushing, the feedstream was loaded onto the membrane and a variable amount was loaded at a constant flow rate of 333-2667 MV/hour. During the load phase the flow through was sampled as necessary. The membrane was then optionally chased with buffer to collect any residual product. To maintain retention of impurities on the membrane, the chase (a.k.a wash buffer) buffer was generally similar in pH and equal to or lower in conductivity to the feed.

The resulting membrane grab samples, fractions, or pools were then analyzed to determine polypeptide and/or impurity concentrations.

In some cases, the resulting membrane pools were then loaded onto a resin. Resin chromatography was only performed using an Äkta Explorer so that UV, pH, and conductivity could be trended real-time and pooling could be facilitated by the in-line UV sensor. During the load phase the flow through was sampled as necessary.

In some cases the membrane was eluted. Membrane elution was only performed using the Akta Explorer so that pooling could be facilitated by the in-line UV sensor. The membrane was eluted using a high salt buffer (20 mM sodium acetate and 350 mM sodium chloride, pH 5.5). Additionally, in some cases the membrane was eluted with a gradient of two buffers, (20 mM sodium acetate, 0 mM sodium chloride, pH 5.5 and 20 mM sodium acetate, 2000 mM sodium chloride, pH 5.5) from 0-100%/over 20 mL.

In some cases the resin was eluted. Resin elution was only performed using the Äkta Explorer so that pooling could be facilitated by the in-line UV sensor. The resins were eluted using a high salt buffer gradient (50 to 500 mM sodium acetate, pH 5.5) or a high salt step (50 mM HEPES, 200 mM sodium chloride, 0.05% Triton, 1 mM DTT, pH 7.5) at a constant flow rate of 200 cm/hr and was pooled from 0.5-1.0 OD or 1.25-1.25 OD for the Fractogel SE Hicap and SP Sepharose Fast Flow, respectively.

Results

Small-Scale Cation Exchange Membrane Yield

Figure 3:
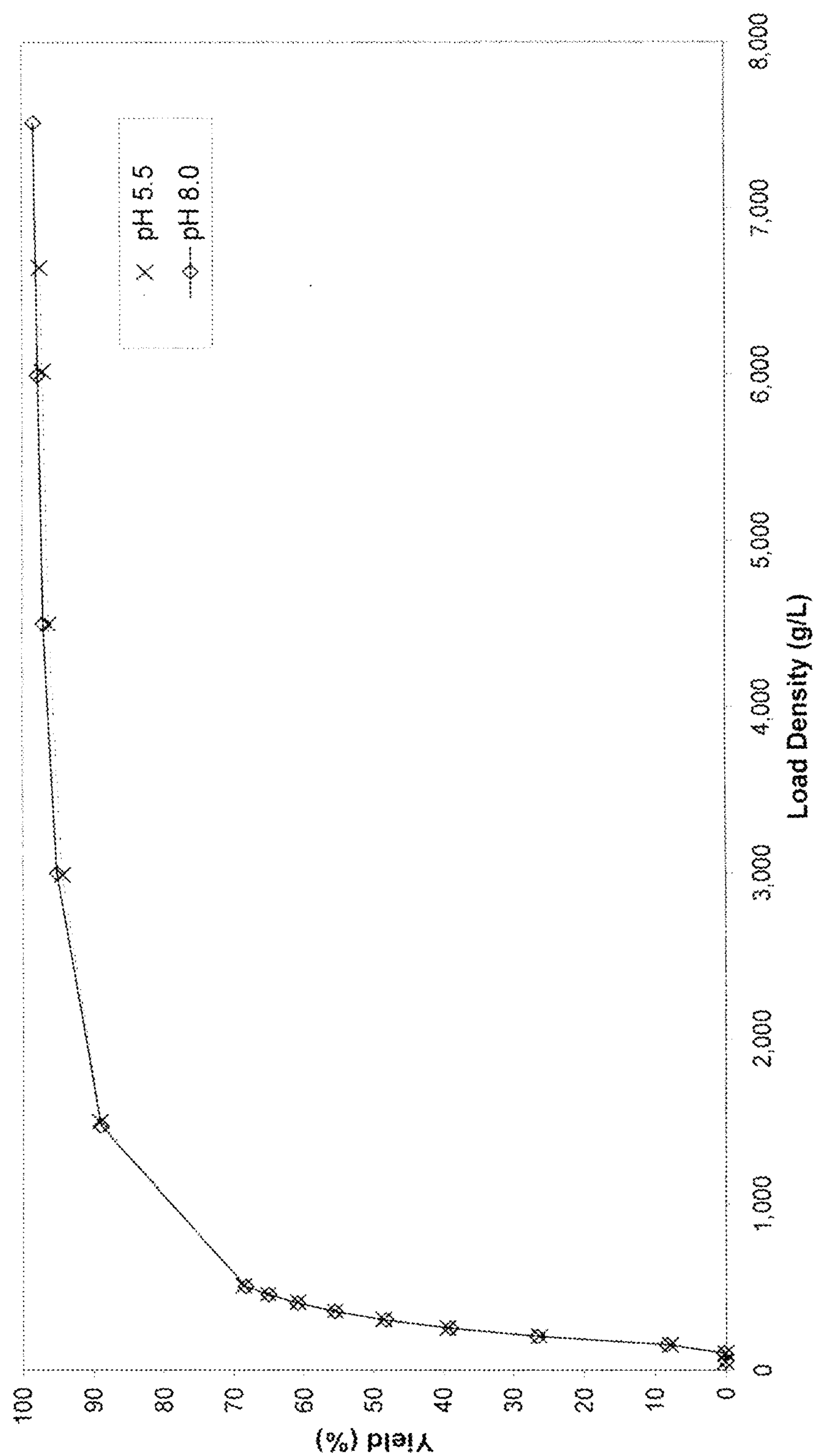
FIG. 3. Yield for mAb 1 anion exchange pool at pH 5.5 and 6.4 mS/cm and at pH 8.0 and 5.0 mS/cm, Mustang™ S (Small-scale, 0.18 mL MV, 667 MV/hour).

MAb 1 anion exchange pool at pH 8.0 and 5.0 mS/cm and mAb 1 anion exchange pool that was adjusted to pH 5.5 and 6.4 mS/cm using IM citric acid, were proccssed over a Mustang™ S membrane at 667 MV/hour. The Mustang™ S membrane used was a 0.18 mL Acrodisc® device. The mAb 1 feedstreams at pH 5.5 and pH 8.0 were both below the pI of the antibody, and therefore positively charged. Feed and flow through grab samples were analyzed for antibody concentration. Although initial samples show some antibody binding to the membrane, FIG. 3 shows yield is similar at both pH conditions, increased rapidly under 1000 g/L load density, and ≥96% is attainable after a load density of approximately 5000 g/L.

Small-Scale Anion Exchange Membrane Yield

Figure 4:
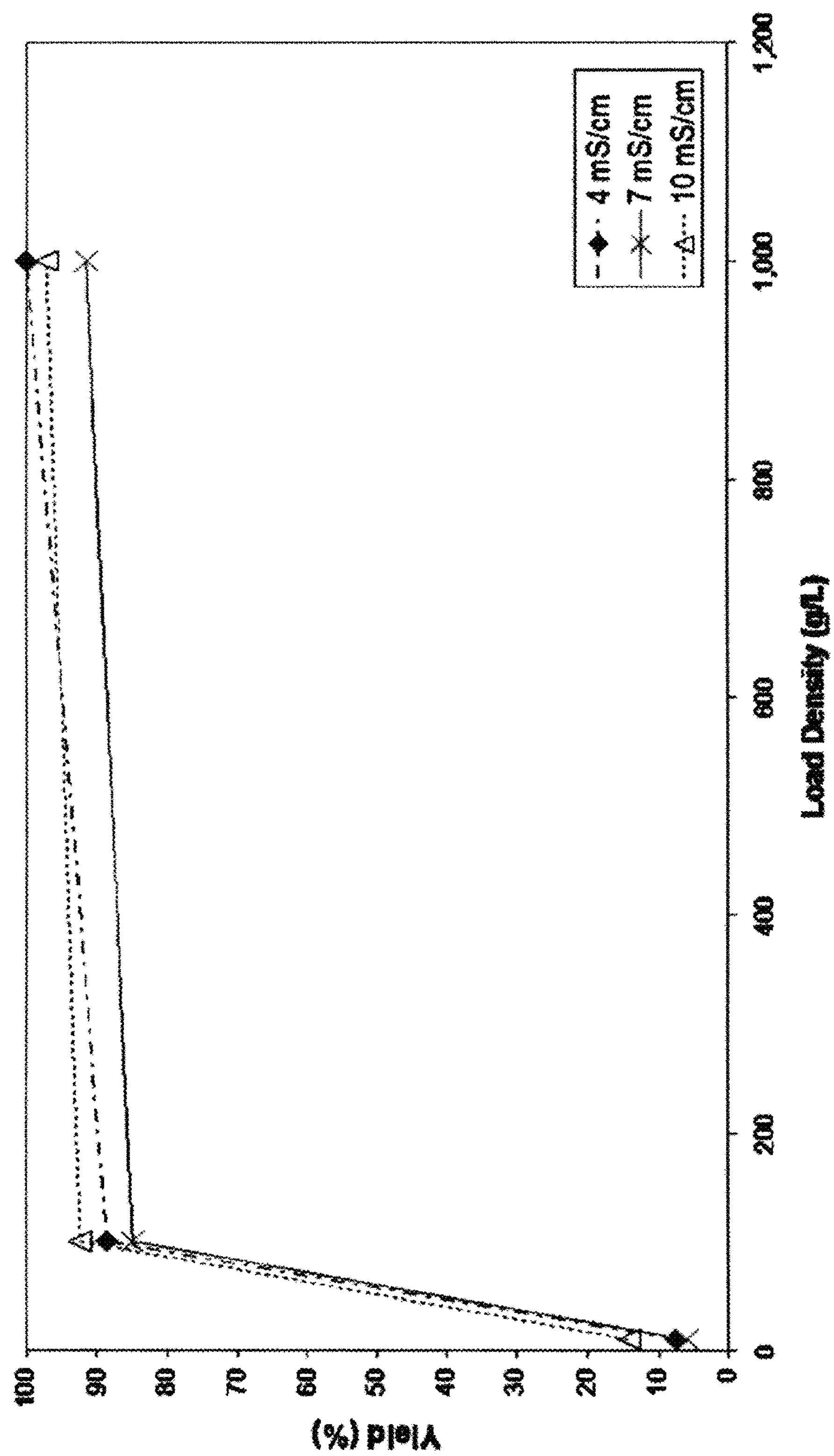
FIG. 4. Yield for mAb 2 cation exchange pool at pH 8.0, Mustang™ Q (Small-scale, 0.35 mL MV, 600 MV/hour).

For comparison purposes mAb 2 was selected for testing using an anion exchange membrane above the isoelectric point of 7.7. Proteins are prone to deamidation and aggregation at high pH so similar tests were not performed on mAb 1. Cation exchange pool at pH 5.5 and 9 mS/cm was pH adjusted to 8.0 using 1.5 M tris base. The feedstock was then split into three separate pools and conductivity was adjusted using purified water. The first pool was at 10 mS/cm, the second and third pools were adjusted to 7 mS/cm and 4 mS/cm, respectively. All three pools were maintained at pH 8.0. Each feedstream was then processed over a small-scale 0.35 mL Mustang™ Q at constant flow rate of 600 MV/hour. The mAb 3 at pH 8.0 was 0.3 pH units above the pI and therefore the antibody was negatively charged. Load and flow through pools were analyzed for antibody concentration. FIG. 4 shows yield is similar at all three pH conditions, increased rapidly initially under 200 g/L load density, and ≥96% after approximately 1000 g/L load density.

Small-Scale Cation Exchange Membrane Impurity Clearance

Figure 5:
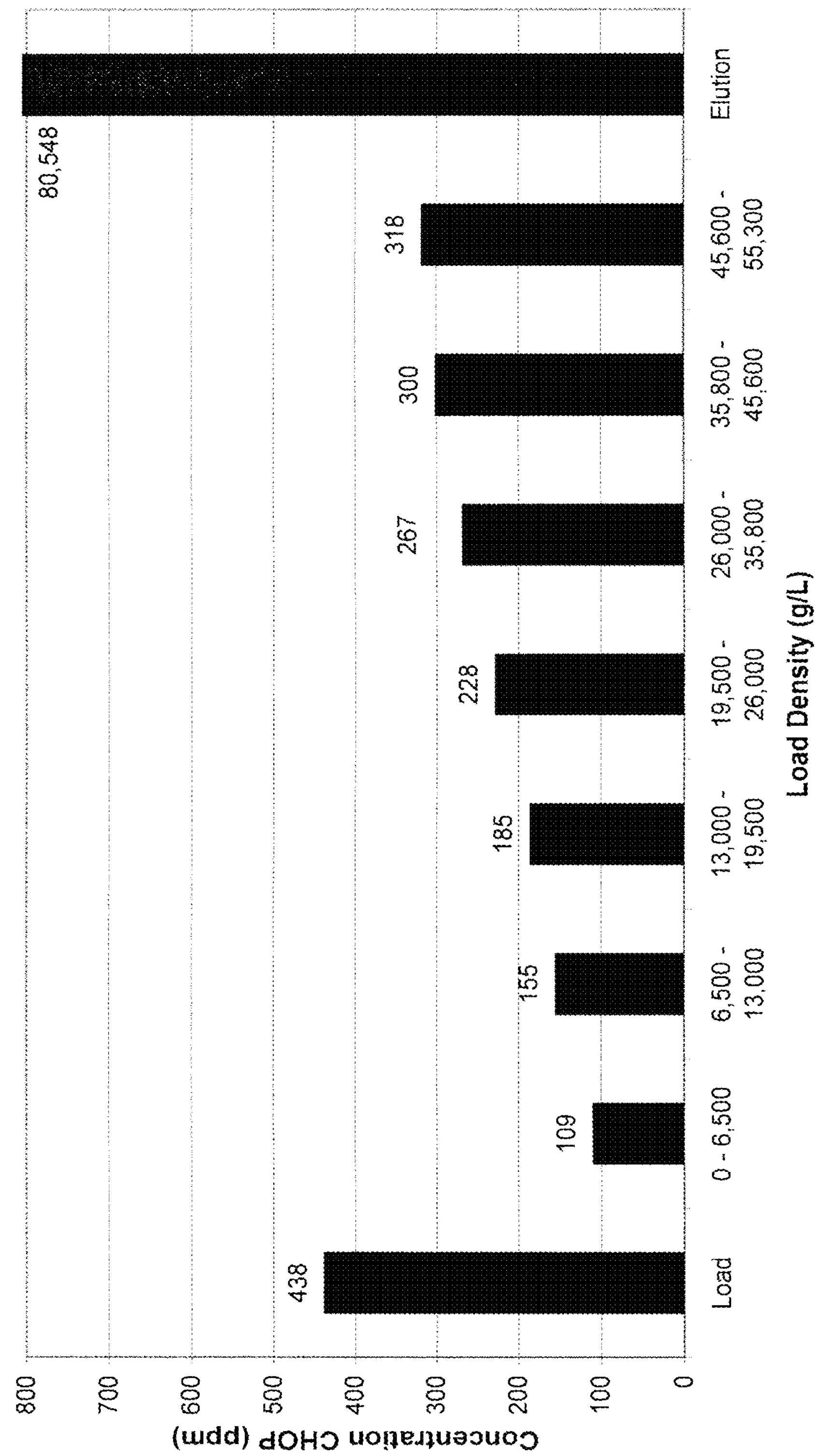
FIG. 5. CHOP clearance for mAb 3 Protein A pool at pH 5.5, 3.2 mS/cm, Mustang™ S (Small-scale, 0.18 mL MV, 1333 MV/hour).

To evaluate cation exchange membrane impurity clearance, mAb 3 Protein A pool at pH 5.5 and 3.2 mS/cm was processed over a small-scale 0.18 mL Mustang™ S membrane at a constant flow rate of 1333 MV/hour. The mAb 3 load was 3.4 units below the calculated pI and therefore the antibody was positively charged. Load, flow through fractions, and elution samples were analyzed and the results for CHOP are shown in FIG. 5. The data show the Mustang™ S initially reduced CHOP from 438 to 109 ppm. CHOP increased to 318 ppm as load density approached 55,300 g/L. The membrane was eluted using a solution containing high salt. The salt ions are used to shield the charges, thus disrupting the electrostatic interactions and causing the proteins to desorb from the membrane surface and move freely into the mobile phase. Analysis of the elution pool shows an enrichment of impurities confirming that CHOP bind to the membrane due to electrostatic forces.

Figure 6:
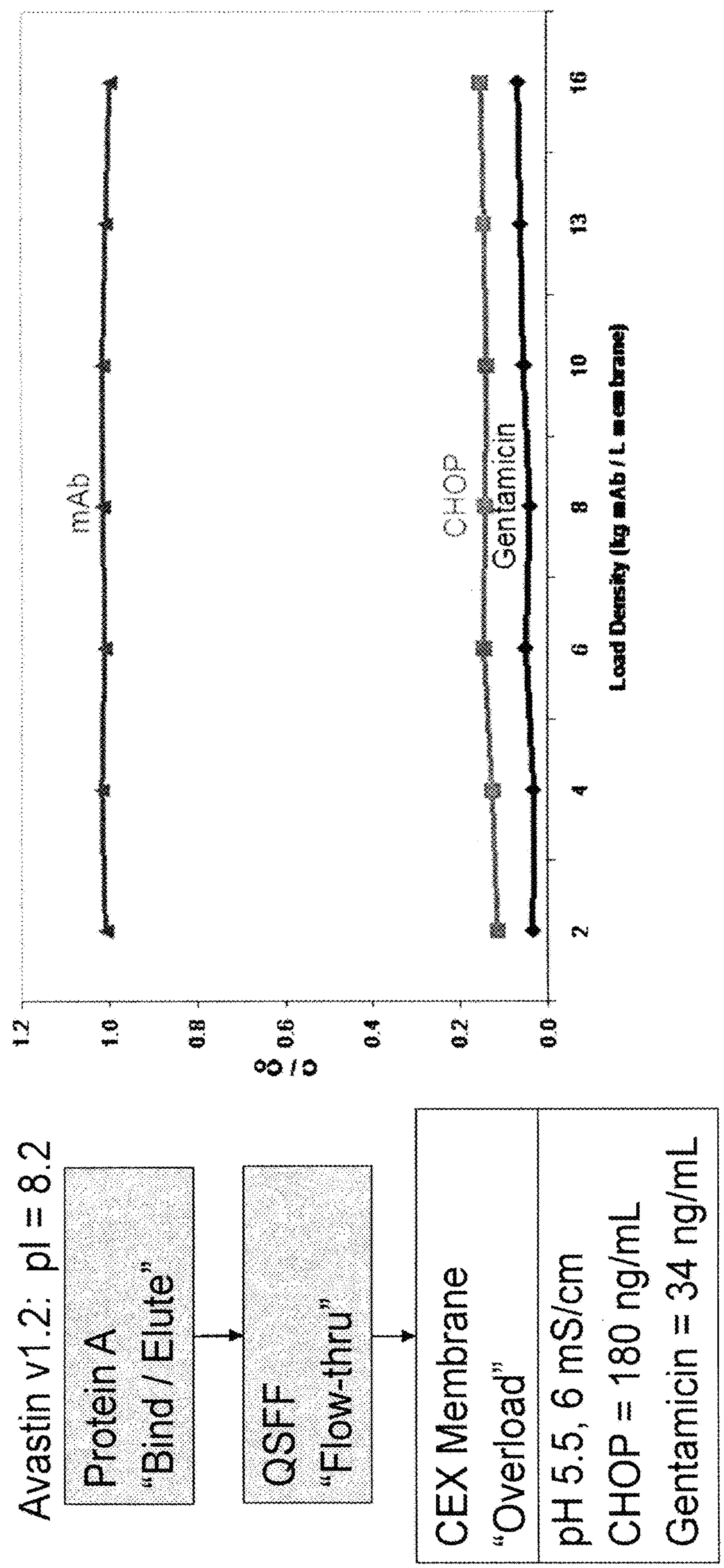
FIG. 6. Clearance of impurities after overload with CEX membranes.

To further evaluate adsorber performance, mAb 3 anion exchange pool at pH 5.5 and 6.0 mS/cm was processed over a small-scale 0.18 mL Mustang™ S membrane at a constant flow rate of 667 MV/hour. The mAb 3 pH was 3.4 pH units below the pI and therefore the antibody was positively charged. Feed and flow through grab samples were analyzed for mAb, CHOP, and gentamicin concentrations. To compare the feed and grab sample concentrations, a $C/C_0$ graph (grab sample/load) as a function of membrane load density was generated. As shown in FIG. 6, mAb $C/C_0$ values are near 1.0 from 2 to 16 kg/L load densities, suggesting that the grab sample concentrations are nearly identical to the load concentration, and once again yield would be high. Conversely, the CHOP and gentamicin $C/C_0$ values are low, at ≤0.2 from 2 to 16 kg/L load densities, suggesting that the grab sample concentrations are much lower than the load concentration and the Mustang™ S is removing the majority of these impurities despite being overloaded with mAb.

Small-Scale Cation Exchange Membrane Binding Selectivity

Figure 7:
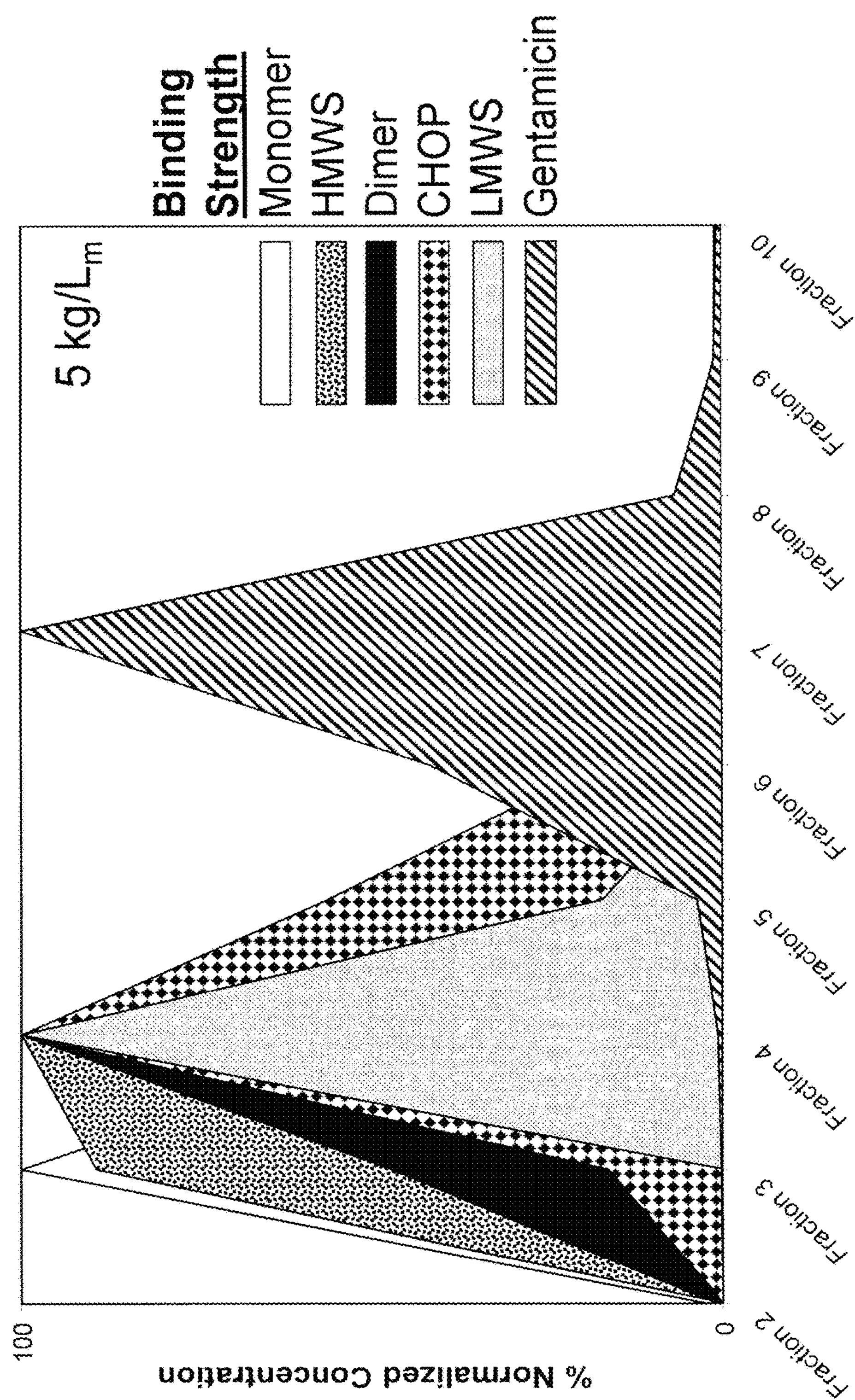
FIG. 7. Mustang S binding strength of various species as determined by gradient elution and normalizing to highest species concentration in each fraction.

To evaluate whether the cation exchange membranes are selective for binding certain impurities versus mAb, a series of experiments were designed and executed using mAb 3 Protein A pool. This pool was chosen due to its higher level of impurities, including high molecular weight species (HMWS), dimer, low molecular weight species (LMWS), gentamicin, and CHOP. The Protein A pool was adjusted to pH 5.5 and 4.4 mS/cm. Prior to loading, each Mustang™ S membrane was equilibrated with 20 mM sodium acetate, pH 5.5 and 1.3 mS/cm buffer. Four experiments were performed, each loading a 0.18 mL Mustang™ S membrane at 1333 MV/hour to load densities of 1000, 5000, 10000, or 15000 g/L. After loading, the membranes were washed with 20 mM sodium acetate, pH 5.5 and 1.3 mS/cm buffer. After washing, a gradient elution using wash buffer and 20 mM sodium acetate, 2M sodium chloride, pH 5.1 and ~500 mS/cm was used to elute the membrane. The gradient was formed over 20 mL, and elution fractions were taken every 2 mL to be analyzed. For the four experimcnts, the elution fractions were analyzed for all impurities and mAb concentrations. At any given load density experiment, the fractions could be compared to determine when an impurity or mAb was eluting from the membrane, with later eluting species being bound more tightly than earlier eluting species. FIG. 7 shows the % normalized concentrations of the various species analyzed across the 10 fraction elution for the 5000 g/L load density experiment The position of each peak suggests that mAb monomer is binding the weakest to the membrane since it elutes earliest. In increasing order of binding strength, monomer is followed by HMWS, Dimer, CHOP, LMWS, and gentamicin. Although many species are eluting at a similar position in the gradient, this graph clearly shows gentamicin binds much stronger than the competing species.

Figure 8:
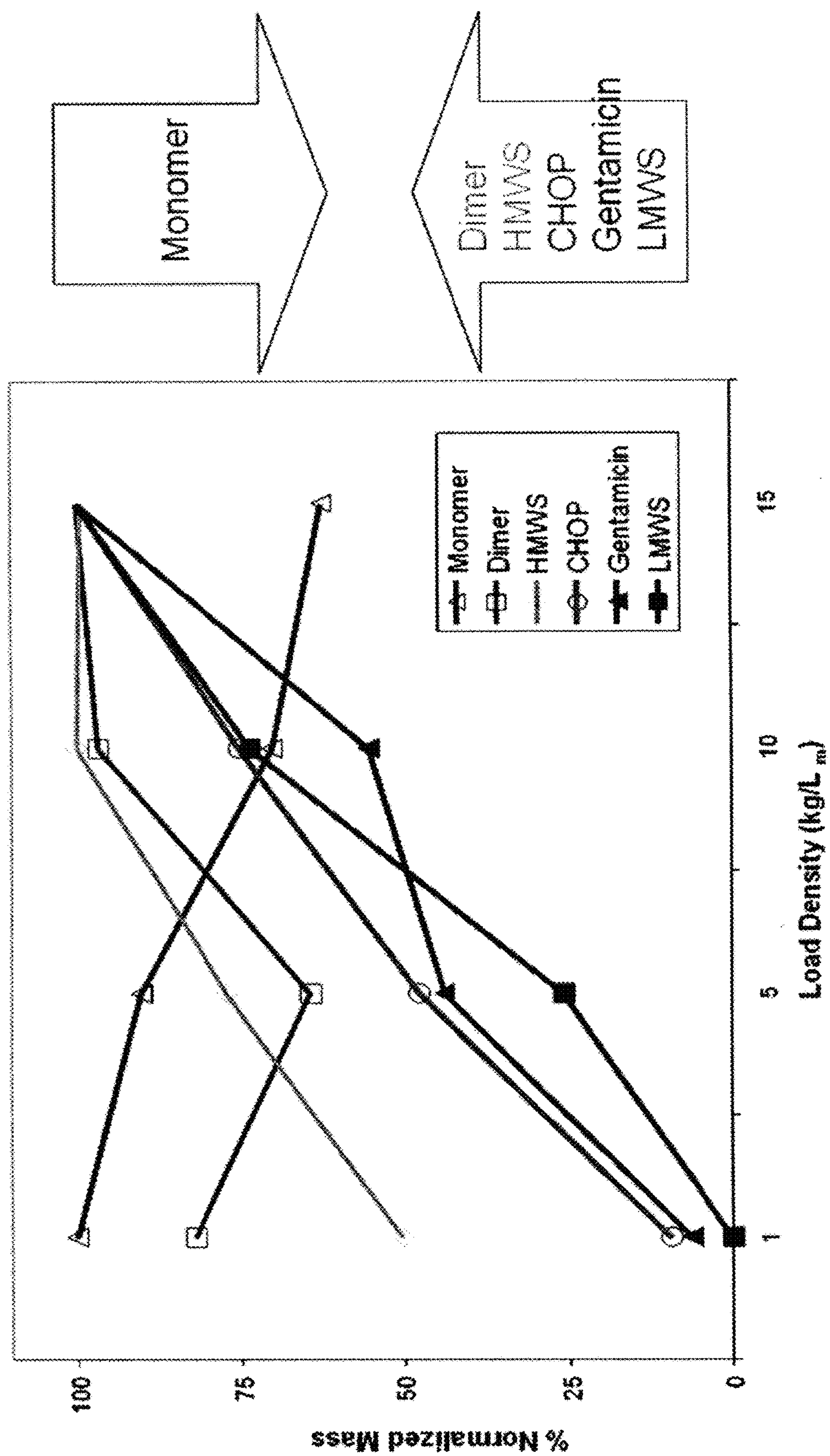
FIG. 8. Mustang S total bound mass of various species as calculated by the summation of all gradient elution fraction masses and compared at different membrane load densities and normalizing to maximum mass.

Additionally, for each load density, the total mass of each impurity or mAb bound to the column could be calculated, and compared across the various load density experiments. FIG. 8 shows the % normalized mass of each species as a function of increasing membrane load dcnsity. The direction of the lines indicates whether the species' mass is increasing or decreasing. mAb monomer, which was previously shown to bind the weakest, has decreasing levels of mass as load density increases. Conversely, dimer, HMWS, CHOP, gentamicin, and LMWS are all increasing in mass as load density increases. This confirms the previous binding strength results and suggests that mAb monomer is decreasing due to other species continually binding to the membrane.

Small-Scale Cation Exchange Membrane Displacement

Figure 9:
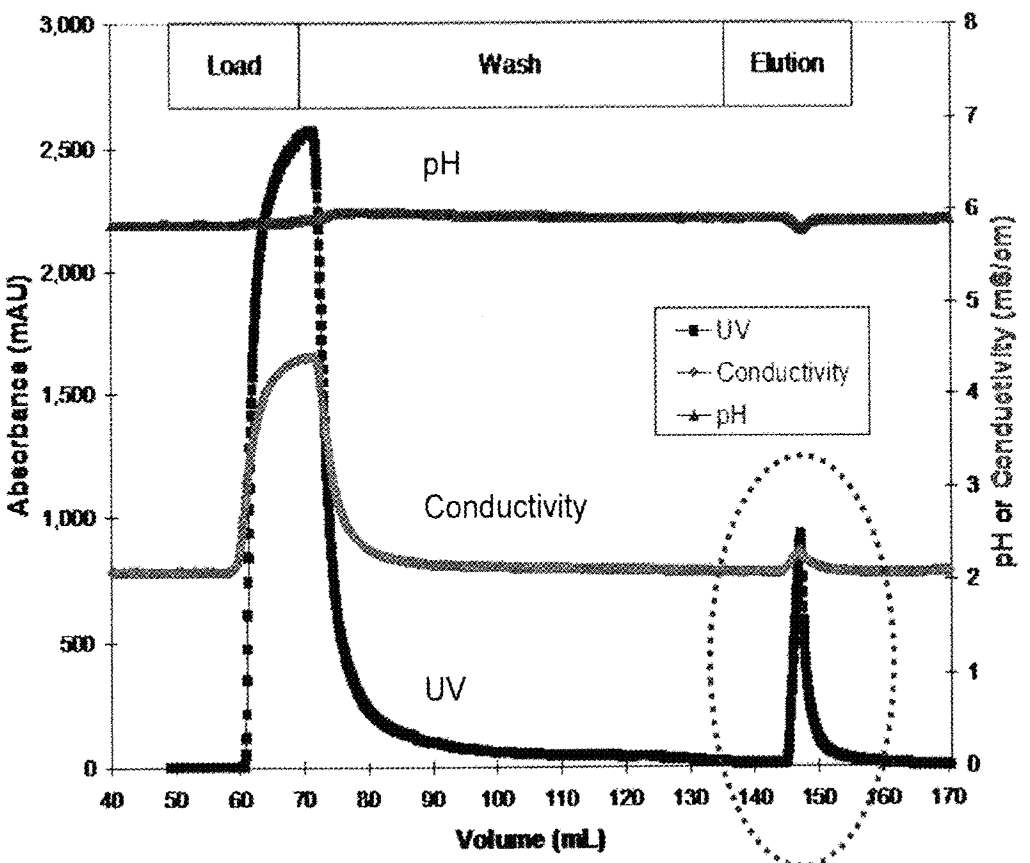
FIG. 9. Mustang S membrane loaded with protein, washed with 20 mM acetate buffer until UV absorbance reaches baseline, and then eluted with 20 mM acetate/gentamicin buffer to demonstrate antibody displacement by gentamicin.

To determine if a strong binding species such as gentamicin can elute mAb monomer, as a hypothesis to explain the binding selectivity results, an experiment was performed using mAb 3 Protein A pool. The Protein A pool was adjusted to pH 5.5 and 4.2 mS/cm. The experiment was performed by equilibrating the 0.18 mL Mustang$^{rM}$ S membrane with 20 mM sodium acetate, pH 5.4. The mAb 1 Protein A pool was loaded until the UV trend clearly showed mAb breakthrough. The membrane was then washed with equilibration buffer before an elution buffer comprised of equilibration buffer and 2 g/L gentamicin was used to elute the membrane. It should be noted that the equilibration buffer and elution buffer were of identical pH and conductivity to prevent any effects on mAb binding to the membrane. FIG. 9 shows the chromatogram, including UV, pH, and conductivity trends, during the load, wash, and elution phases. The chromatogram shows that the wash phase was sufficient in returning the UV trend to baseline before the elution phase was initiated. It also shows that during the elution phase, a large UV peak is observed without any significant change to the pH or conductivity trends. This demonstrates that gentamicin can effectively displace bound mAb monomer from a cation exchange membrane.

CEX Membranes Gentamicin Binding Comparison

To determine the CEX membrane binding capacity of gentamicin, experiments were performed testing the 0.18 mL Mustang™ S membrane and the 0.23 mL Natrix S. A PBS buffer at pH 7.2 was adjusted with 2.0M acetic acid and PW to a final pH of 5.00 and conductivity of 8.10 mS/cm. The adjusted buffer was then spiked with mAb 3 UF/DF pool and gentamicin to final concentrations of approximately 1.0 mg/mL and 40,000 ng/mL. The resulting spiked solution was used as the load feedstream.

Figure 10:
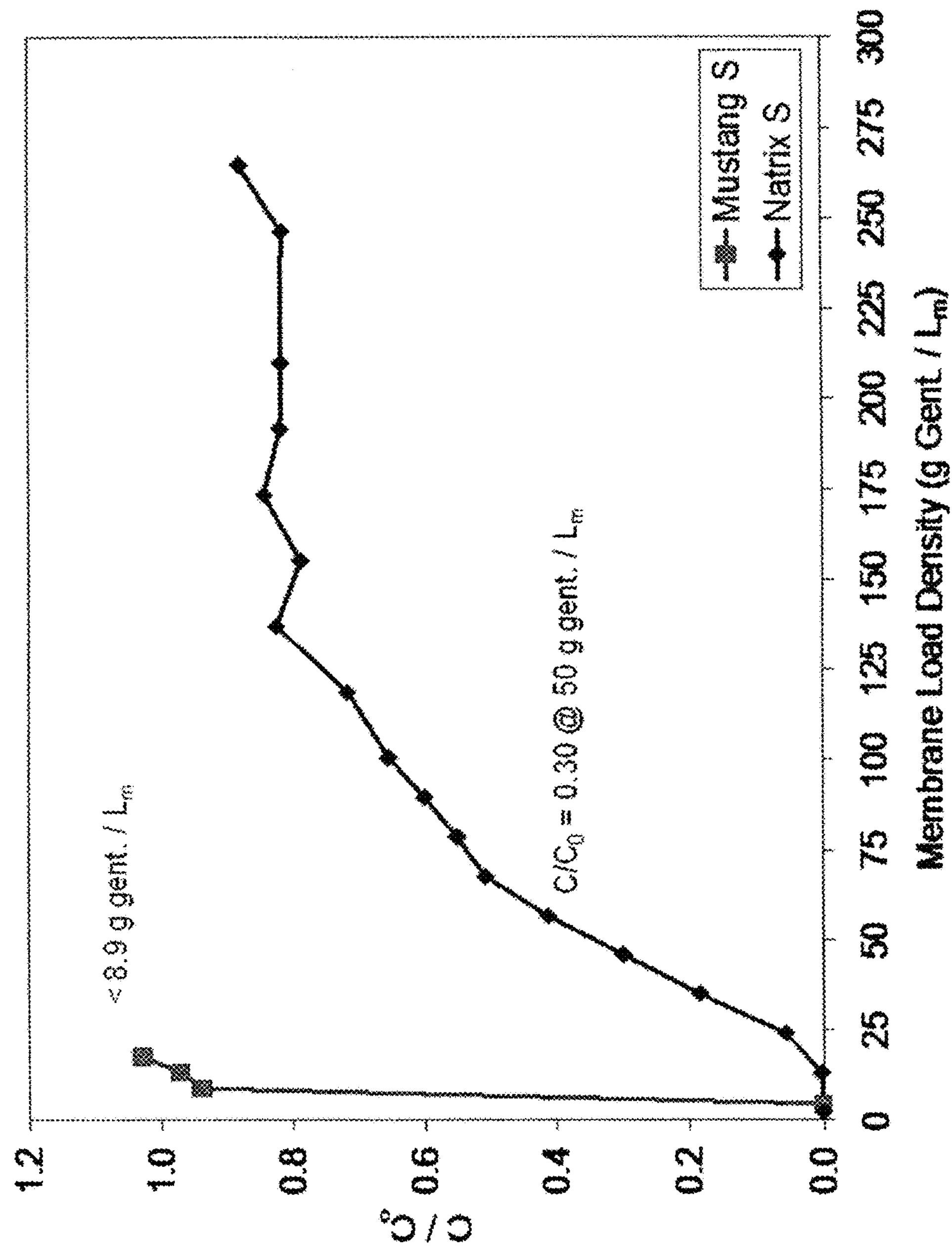
FIG. 10. Outline depicting protocol for determining antibody dynamic binding Capacity (DBC) on a CEX column (Fractogel SE Hicap) with or without utilizing CEX membrane at various gentamicin concentrations.

To perform the experiments, both membranes were flushed with PW, equilibrated with the adjusted buffer, loaded with the spiked solution, and washed with the adjusted buffer. During the loading phase, 4 mL flow-through grab samples were collected for the Mustang™ S at 20, 40, 60, and 80 mL. For the Natrix S, a 4 mL flow-through grab sample was collected at 10 mL and then every 60 mL for a total of 19 samples. All samples were then analyzed for mAb and gentamicin concentration and compared to the load concentrations to create a $C/C_0$ graph versus membrane load density as shown in FIG. 10.

Although not plotted, the mAb concentration reaches a $C/C_0$ value of 1.0, suggesting that the step would be high yielding for antibody in the flow-through. Gentamicin $C/C_0$ values, conversely, reach 1.0 much later, suggesting that both membranes are binding significant levels. The Mustang™ S had a gentamicin binding capacity between 4.4 and 8.9 g/L, while the Natrix S had a higher gentamicin binding capacity and showed slower breakthrough. At 50 g/$L_m$ the $C/C_0$ value was 0.3 and the breakthrough curve was somewhat linear up to about 125 g/Lm and a $C/C_0$ value of about 0.8. After 125 g/$L_m$ the breakthrough curve flattens out suggesting that the membrane may still be binding gentamicin while possibly displacing small levels of mAb.

These results show that different CEX membranes have different gentamicin binding capacities and breakthrough curves. The Natrix S, with its higher binding capacity and gradual breakthrough, would make a more effective membrane for removing gentamicin. Additionally, by binding higher levels of gentamicin, it would be expected that more mAb is displaced, resulting in a higher yielding operation.

CEX Resins and the Effects of Strongly Binding Aminoglycoside Antibiotics

Figure 11:
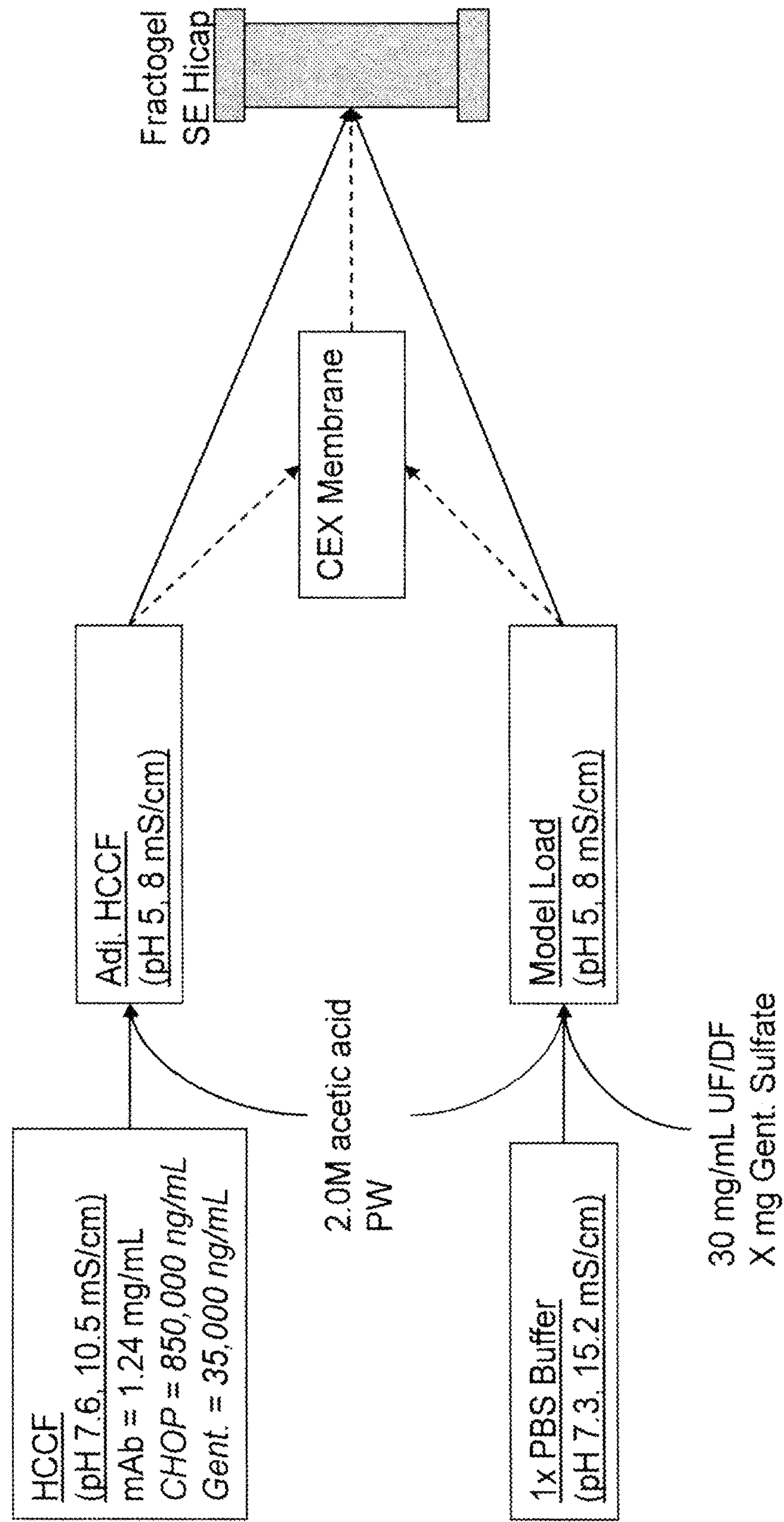
FIG. 11. Effect of gentamicin concentration on Fractogel SE Hicap antibody DBC.

To determine what effect a strongly binding impurity such as gentamicin may have on a packed column of CEX resin, a series of experiments were designed to test both model feedstreams and actual feedstreams, with or without a CEX membrane protecting the column. FIG. 11 shows the various experiments, antibody and impurity concentrations, and steps needed to perform these experiments.

First, using a model feedstream of PBS spiked with mAb 3 UF/DF pool and varying levels of gentamicin, a Fractogel SE Hicap resin was tested for antibody binding capacity by generating breakthrough curves. The PBS was first adjusted with 1.0M acetic acid to pH 5.0, then adjusted with PW to a conductivity of 8.0 mS/cm. The UF/DF pool was spiked into the adjusted buffer to a mAb concentration of approximately 1.6 mg/mL.

For each chromatography experiment performed, the Fractogel SE Hicap was first equilibrated with 25 mM sodium acetate at pH 5 prior to loading with the desired feedstream. After loading, the column was washed with 50 mM sodium acetate at pH 5.5, washed with 25 mM HEPES at pH 7.7, washed with 50 mM sodium acetate at pH 5.5, eluted using 350 mM sodium acetate at pH 5.5, regenerated using 1 M NaCl and 0.5N NaOH, and then stored in 0.1N NaOH until the column's next use.

Without spiking gentamicin, a first experiment was performed and showed an antibody DBC of 108 g/L. Next, the above adjustment and spiking was performed with the addition of gentamicin to a final concentration of 24,100 mg/mL. This experiment showed a decreased antibody DBC of 89 g/L. That condition was repeated with a gentamicin concentration of 30,500, and the antibody DBC of 88 g/L was calculated. This data shows that using a model system of PBS, purified antibody, and varying levels of gentamicin, the presence of gentamicin decreases antibody DBC on the Fractogel SE Hicap resin from 108 mg/mL to approximately 88 g/L.

Next, two experiments were performed using harvested cell culture fluid (HCCF) containing approximately 0.9 mg/mL mAb 3, 24,100-30,000 ng/mL gentamicin, and 408,000 ng/mL CHOP. Using HCCF at gentamicin levels consistent with the model feedstream, antibody DBCs of 68 and 71 g/L. A possible explanation for the difference between the model feedstream DBCs of 88 and 89 g/L and the DBCs of 68 and 71 g/L using HCCF is the presence of high levels of CHOP in the feedstream.

Figure 12:
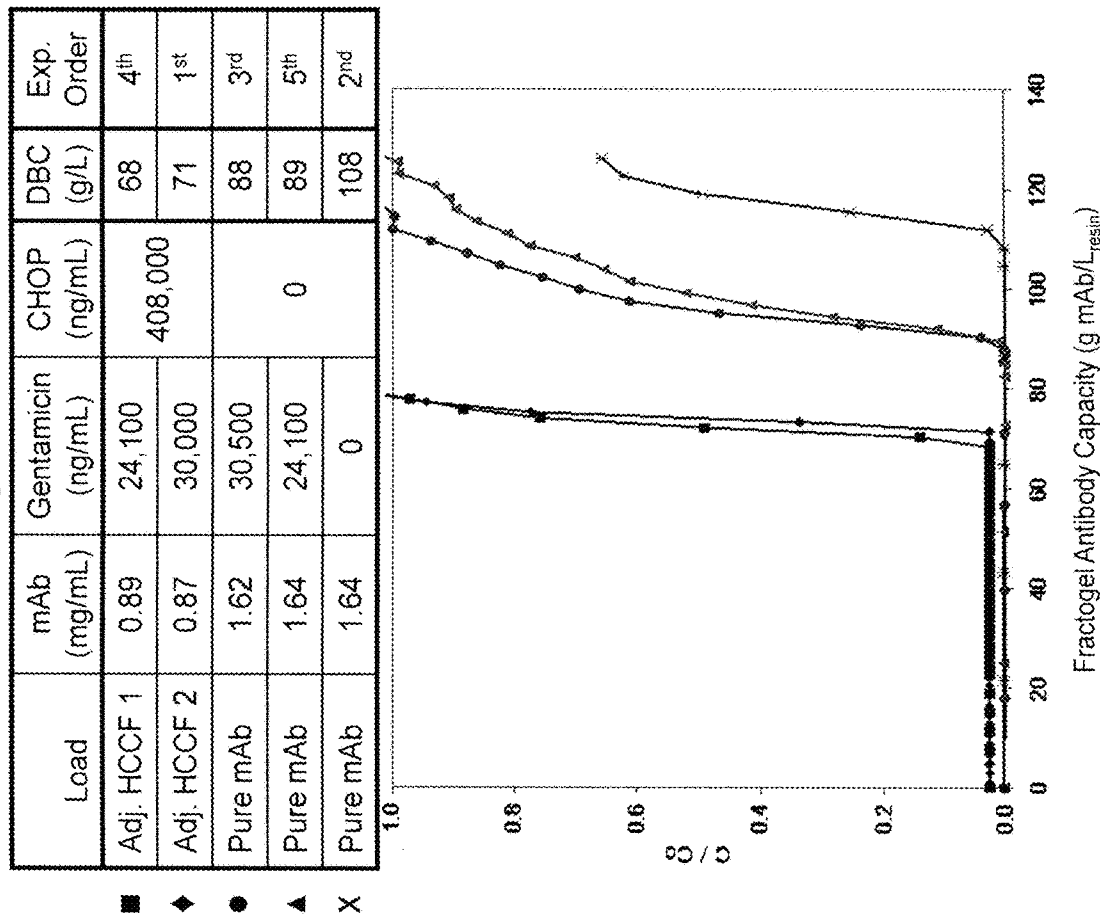
FIG. 12. Comparison of gentamicin DBC on two CEX membranes (Mustang S and Natrix S).

FIG. 12 shows all antibody breakthrough curves from the above mentioned experiments, as well as impurity levels of the feedstream, and approximated DBCs. The runs were also performed in a randomized order to avoid possible degradation of the column or gentamicin carryover from run to run. The order of experiments is listed in the table accompanying FIG. 12. There was no correlation between order of experiments and antibody DBC, so it is unlikely that the column was degrading or that gentamicin carryover was affecting subsequent runs.

Figure 13:
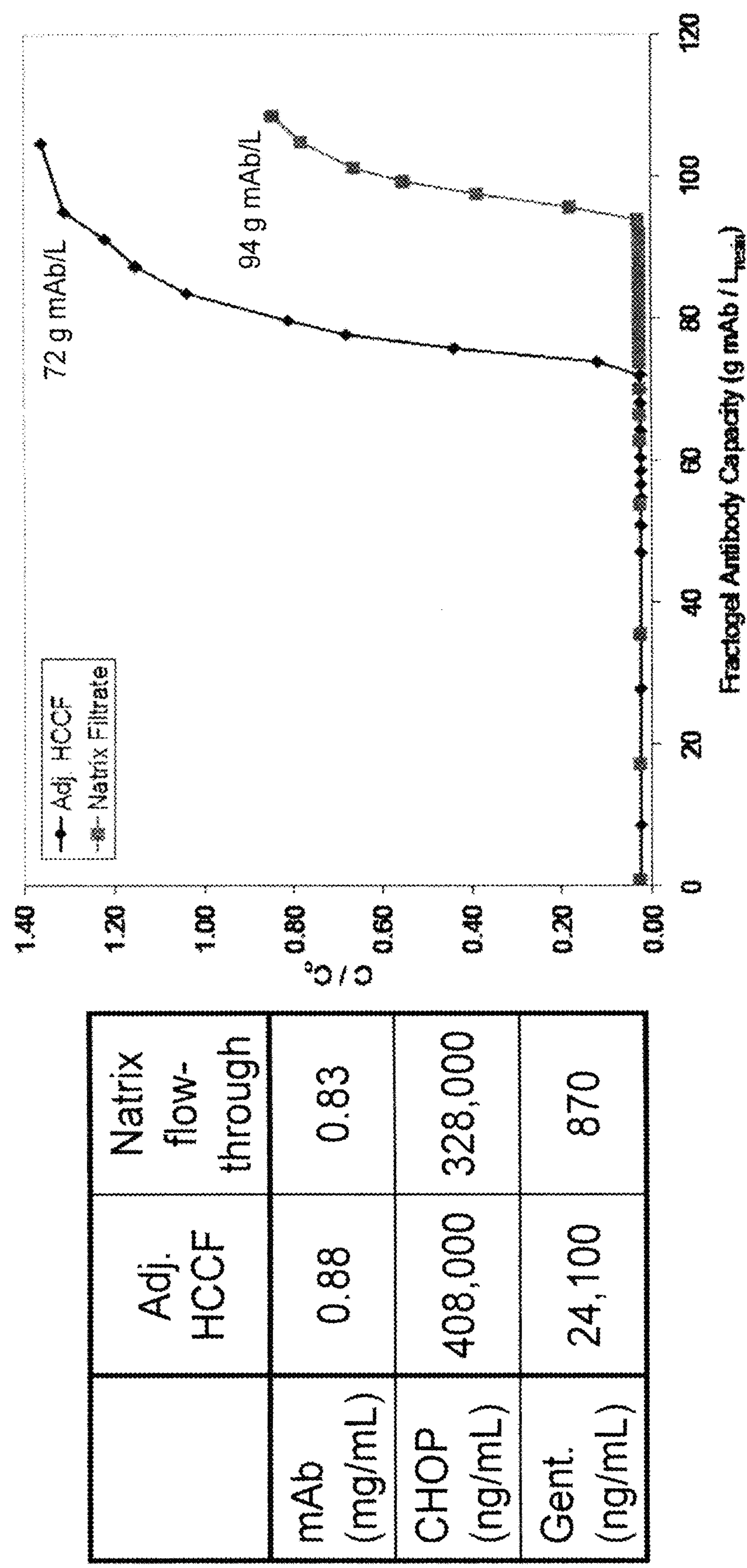
FIG. 13. Fractogel SE Hicap antibody DBC with overloaded Natrix S pool showing 30% DBC improvement.

Finally, knowing that the presence of gentamicin in the feedstream shows a significant decrease in column DBCs and that CEX membranes are able to bind gentamicin without binding significant levels of antibody, two experiments were performed to test whether a CEX membrane could protect and improve performance on a CEX resin. Because the Natrix S showed improved binding capacity of gentamicin over the Mustang™ S it was used to protect the Fractogel SE Hicap. 2 L of HCCF were thawed, adjusted to pH 5 with 2M acetic acid, adjusted to 8 mS/cm with PW, and off-line sterile filtered to remove any effects from the freezing and thawing of the feedstream. From this adjusted and filtered feedstream, the load was split with one portion being loaded onto the column while the other portion was processed through a 0.75 mL Natrix S and then loaded onto the Fractogel SE Hicap. For both column load phases, 15 mL fractions were taken for about 60 samples each. The adjusted HCCF, Natrix flow-through, and Fractogel SE Hicap fractions were analyzed for antibody and gentamicin concentrations. The resulting HCCF and Natrix flow-through feedstream antibody and impurity concentrations, as well as the resulting Fractogcl SE Hicap breakthrough curves arc shown in FIG. 13. The resulting data shows the Natrix successfully reduced gentamicin levels in the adjusted HCCF from 24,100 ng/mL to 870 ng/mL. CHOP levels were slightly decreased from 408,000 ng/mL to 328,000 ng/mL. The antibody concentration was slightly lower at 0.83 mg/mL compared to the adjusted HCCF concentration of 0.88 mg/mL, representing a yield of about 94%. Finally, the resulting CEX column breakthrough curves show column had an antibody DBC of 72 g/L using the adjusted HCCF and an antibody DBC of 94 g/L using the Natrix flow-through. This represents an approximate 30% increase in DBC by passing a gentamicin containing feedstream through a CEX membrane prior to loading on the CEX column.

CEX Membrane ECP and PEI Breakthrough

Figure 14:
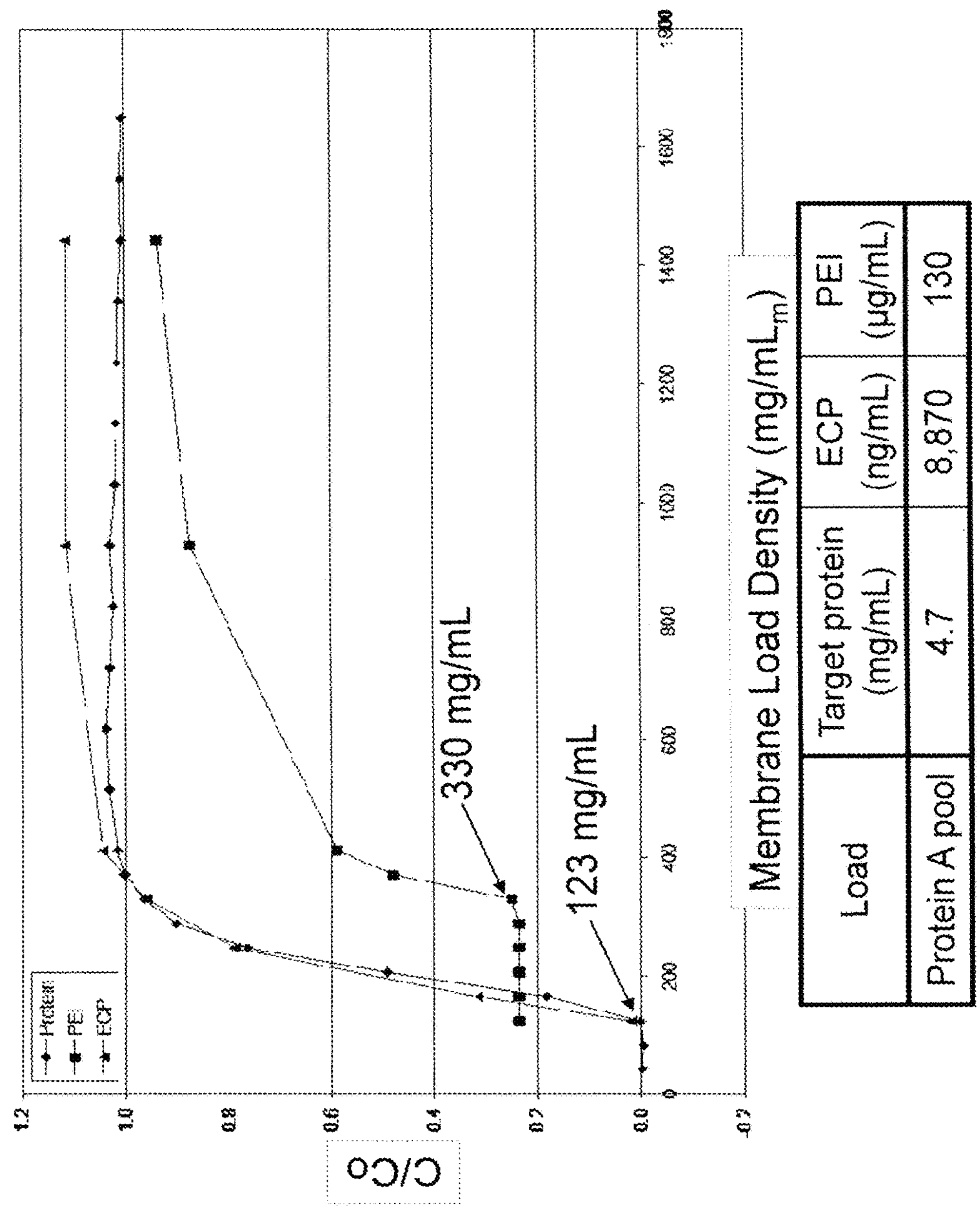
FIG. 14. Eftfect of PEI % used in extraction process on SP Sepharose Fast Flow (SPSFF) protein DBC showing 36 to 51 g/L improvement as less PEI is used.

To test whether similar performance could be observed using a CEX membrane with other impurities, such as ECPs or PEI, an experiment was performed using Monovalent Antibody 1 Protein A pool and a 0.23 mL Natrix S membrane. The Protein A pool used had been previously adjusted to pH 6.7 using 1.5M TRIS base, and diluted to a conductivity of 2.5 mS/cm using PW. The load, which had an antibody concentration of 4.7 g/L, 130 ug/mL PEI, and 8,870 ng/mL ECP, was loaded onto an equilibrated Natrix S and flow-through fractions of 2 mL for 10 samples followed by 5 mL fractions for 12 samples were taken. The flow-through fractions were then analyzed for antibody, PEI, and ECP concentration which were then used to generate a $C/C_0$ versus the membrane's antibody load density. FIG. 14 shows that both antibody and ECPs break through the CEX membrane at approximately 123 mg/mL. Because the PEI level of quantification is 30 ug/mL, the first few samples were at or below that level, and FIG. 14 shows a $C/C_0$ value of 0.23 since it was unknown what concentration of PEI exists in those samples. Disregarding the PEI levels at 0.23, PEI appears to break through at 330 mg/mL, significantly later than both antibody and ECPs. These results suggest that CEX membranes are also effective in removing ionic polymers without negatively effecting antibody yield.

CEX Resins and the Effects of Strongly Binding Ionic Polymers

To determine what effect a strongly binding impurity such as PEI may have on a packed column of CEX resin, a series of experiments were performed evaluating the levels of PEI used during the extraction of Polypeptide 1 and their effect on a SP Sepharose Fast Flow column. Because the feedstream was more impure for this product, it was not possible to quantify the PEI levels going onto the column, instead the levels of PEI used during extraction were noted.

Figure 15:
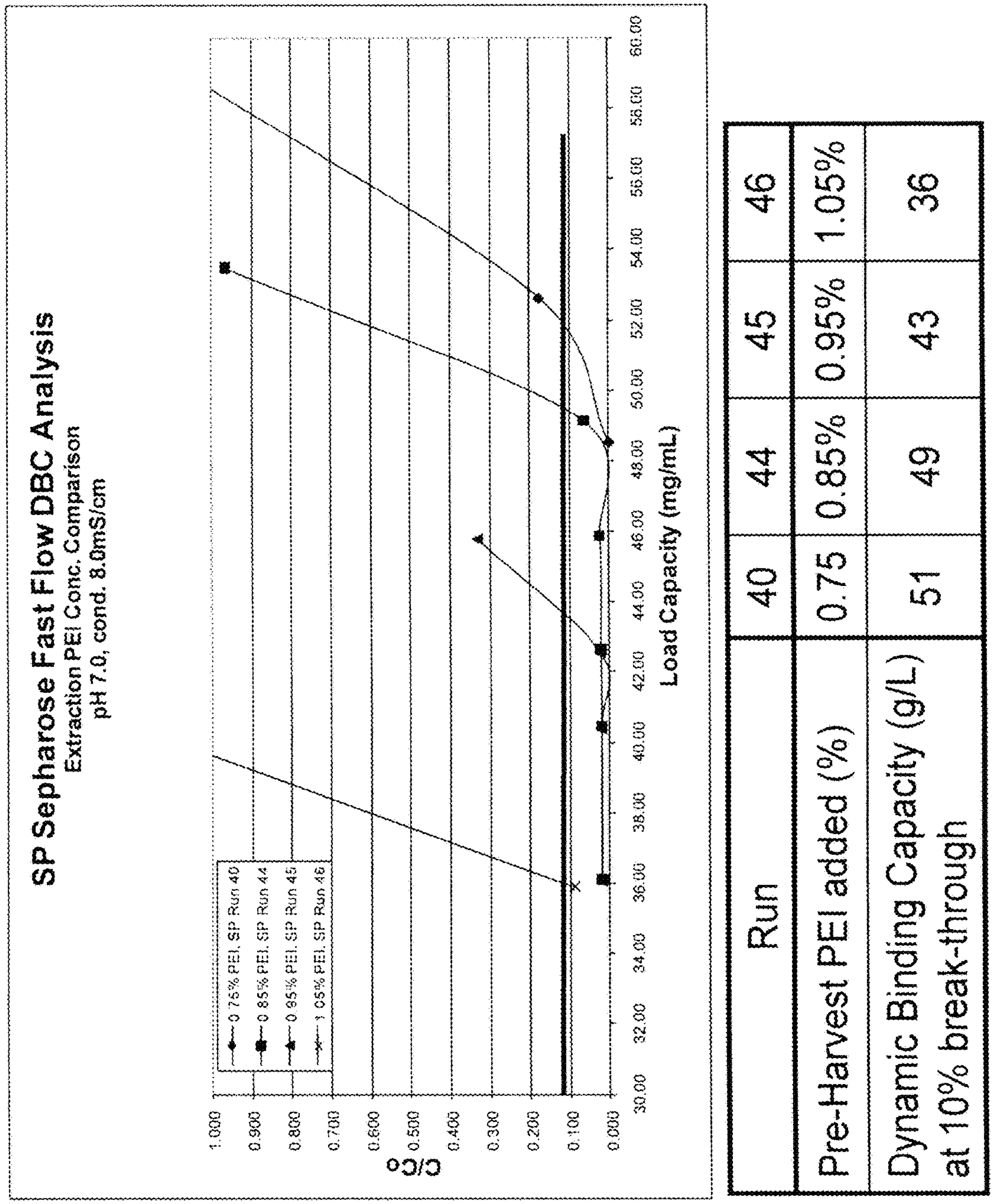
FIG. 15. Effect of PEI % using in extraction process on SPSFF showing decreased step yield and increased pool impurities as more PEI is used.

For these experiments, the extracted product was conditioned with varying levels of PEI ranging from 0.75 to 1.05%, diluted with PW, and centrifuged to produce 4 centrate samples. Each centrate sample, at approximately pH 7.0 and 8.0 mS/cm was then loaded onto the SP Sepharose Fast Flow column with flow-through samples collected and analyzed for polypeptide concentration. The resulting data was used to generate a $C/C_0$ graph as a function of resin polypeptide load density. FIG. 15 shows the breakthrough curves and the corresponding DBC of the column for each centrate tested. As shown in the table, as PEI % increases during the extraction process, the column's DBC decreases.

Additionally, on a second set of experiments using Polypeptide 1, centrates of varying PEI % were loaded onto the SP Sepharose Fast Flow column, with the column subsequently being washed and eluted for each experiment. The resulting pools from each experiment were then analyzed for polypeptide concentration, ECPs, and product size by size exclusion chromatograph. FIG. 16 shows that the pools generated using increasing levels of PEI % during extraction result in decreases in step yield and the pool increasing levels of impurity, such as ECPs, product aggregates, or dimers.

Although experiments were not performed using a CEX membrane prior to this CEX column, knowing that PEI can be bound by the Natrix S from previous experiments and seeing the decreased CEX column's performance as a function of PEI %, it could be hypothesized that using a CEX membrane on this feedstream would improve not only the binding capacity of the column, but also the resulting pool.

CONCLUSION

Ion exchange membranes were shown to be effective at removing impurities at pH and conductivity conditions that cause protein binding. By operating via overload chromatography and promoting competitive adsorption between impurities and the protein of interest, yields were shown to be ≥96% after load densities of 1000-5000 $g/L_m$ were achieved. Cation exchange membranes were shown to bind and significantly reduce impurities such as CHOP and gentamicin in the membrane flow through fractions, with $C/C_0$ values <0.2 to load densities of 16,000 $g/L_m$. The cation exchange membranes were also shown to exhibit selectivity for binding certain impurities versus antibody using more crude feedstreams containing high molecular weight species, dimer, low molecular weight species, gentamicin, and CHOP. In these studies, it was shown that these impurities bind with varying strength, increasing membrane load densities show continued binding of impurities while antibody bound to the membrane decreases, and small molecular weight, highly charged species such as gentamicin bind much stronger than the competing species. Furthermore, competitive adsorption and displacement chromatography were confirmed to occur by eluting antibody from a cation exchange membrane using buffer containing gentamicin. Two cation exchange membranes, the Mustang™ S and Natrix S, were shown to have dynamic binding capacities for gentamicin of 4.4-8.9 g/$L_m$ and 50 g/$L_m$, respectively. The breakthrough curve for the Natrix S was also shown to be more gradual than the Mustang™ S. The Natrix S is designed to have higher binding capacities than traditional membranes, and this property along with the gradual breakthrough makes it well suited for clearing impurities.

Cation exchange resins were shown to exhibit varying dynamic binding capacities in the presence of gentamicin, with DBC decreasing as gentamicin concentrations in the feedstream increase. A Fractogel SE Hicap column decreased in DBC from 108 to 88 g/L using a model feedstream containing 0 to 30,500 ng/mg gentamicin. Using a representative feedstream, the Fractogel SE Hicap showed DBCs of 68-71 g/L. The usefulness of a cation exchange membrane was verified when it was able to decrease gentamicin concentrations in that feedstream from 24,100 ng/mg to 870 ng/mg gentamicin with a yield of 94%. The decreased gentamicin concentration feedstream enabled the Fractogel SE Hicap to have a DBC of 94 g/L compared to a 72 g/L when directly compared. Much like gentamicin, cation exchange membranes were shown to bind highly charged ionic polymers such as PEI in the presence of a monovalent antibody and ECPs. Finally, cation exchange resins were shown to be negatively affected by varying PEI concentrations in the feedstream, resulting in decreased dynamic binding capacity and increased pool impurities as PEI concentrations increased. The SP Sepharose Fast Flow column was shown to decrease from 51 g/L to 36 g/L as PEI increases from 0.75% to 1.05% upstream. In a separate study, step yield decreased from 96% to 70%, ECPs increased from 155 ng/mg to 904 ng/mg, aggregate increased from 2.5% to 17.3%, and dimer increased from 3.7% to 5.9% as the PEI concentration used upstream increased from 0.6% to 1.1%. The use of a cation exchange membrane prior to the SP Sepharose Fast Flow column was not tested, but knowing that the column is negatively impacted by PEI and a membrane is effective in binding PEI, a properly sized membrane should reduce PEI % going onto the column leading to higher binding capacities and yield, while also decreasing pool impurity concentrations.

Better purification technologies are constantly emerging. As higher binding capacity ion exchange resins are developed, their use as a Protein A affinity resin alternative seems likely due to decreased operating costs. However, when subjected to feedstreams of increasing impurity levels, or impurities such as gentamicin or PEI not typically observed in downstream applications, their true effectiveness may be decreased. The use of an ion exchange membrane prior to such an ion exchange resin can protect the column by decreasing the impurities loaded onto the column. This can lead to several improvements for the column, such as higher dynamic binding capacities, increased step yields, or decreased pool impurity concentrations. By selecting an appropriate membrane with sufficient impurity binding capacity, volume, and permeability, the two steps may be operated continuously, further reducing operating time and ultimately purification process costs.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of enhancing efficiency of downstream chromatography steps for purification of proteins comprising:

a. passing a composition comprising a polypeptide of interest and one or more contaminants through a cation exchange membrane, wherein the one or more contaminants is one or more of a host cell protein, aminoglycoside antibiotic, nucleic acid, a variant of the polypeptide of interest, another polypeptide, an endotoxin, or a viral contaminant, wherein the polypeptide and the membrane have opposite charge, at operating conditions comprised of a buffer having a pH sufficiently distinct from the pI of the polypeptide to enhance the charge of the polypeptide and a low ionic strength effective to prevent the shielding of charges by buffer ions, which cause the membrane to bind the polypeptide and at least one contaminant;

b. overloading the cation exchange membrane such that at least one contaminant remains bound to the membrane while the polypeptide of interest is primarily in the effluent;

c. collecting the effluent from the cation exchange membrane comprising the polypeptide of interest;

d. subjecting the membrane effluent comprising the polypeptide of interest to a cation exchange chromatography step, and e. recovering the purified polypeptide from the effluent of the cation exchange chromatography step.

2. The method of claim 1 wherein the cation exchange membrane has a pore size of 0.1 to 100 μm.

3. The method of claim 1 wherein the membrane is a mixed mode adsorber.

4. The method of claim 1 wherein the contaminant is a host cell protein.

5. The method of claim 4 wherein the host cell protein is a Chinese Hamster Ovary Protein (CHOP).

6. The method of claim 4 wherein the host cell protein is an *E.coli* protein (ECP).

7. The method of claim 1 wherein the one or more contaminant is an aminoglycoside antibiotic.

8. The method of claim 7 wherein the aminoglycoside antibiotic is gentamicin.

9. The method of claim 1 wherein the polypeptide comprises a CH2/CH3 region.

10. The method of claim 9 wherein the polypeptide is an antibody.

11. The method of claim 10 wherein the antibody is a monoclonal antibody.

12. The method of claim 1 wherein the cation exchange chromatography step runs continuously during steps a through c.

13. The method of claim 1 further comprising preparing a pharmaceutical composition by combining the purified polypeptide with a pharmaceutically acceptable carrier.

14. A method of enhancing efficiency of downstream chromatography steps for purification of proteins comprising:

a. passing a composition comprising a polypeptide of interest and one or more contaminants through a cation exchange membrane, wherein the one or more contaminants is one or more of a host cell protein, aminoglycoside antibiotic, nucleic acid, a variant of the polypeptide of interest, another polypeptide, an endotoxin, or a viral contaminant, wherein the polypeptide and the membrane have opposite charge, at operating conditions comprised of a buffer having a pH of about 1 to about 5 pH units below the pI of the polypeptide and a conductivity of < about 40 mS/cm, which cause the membrane to bind the polypeptide and at least one contaminant, b. overloading the cation exchange membrane such that at least one contaminant remains bound to the membrane while the polypeptide of interest is primarily in the effluent;

c. collecting the effluent from the cation exchange membrane comprising the polypeptide of interest;

d. subjecting the membrane effluent comprising the polypeptide of interest to a cation exchange chromatography purification step, and e. recovering the purified polypeptide from the effluent of the cation exchange chromatography purification step.

15. The method of claim 14 wherein the pH is about 1 to about 4 pH units, about 1 to about 3 pH units, about 1 to about 2 pH units, or about 1 pH unit below the pI of the polypeptide.

16. The method of claim 14 wherein the conductivity is < about 20 mS/cm or about < about 10 mS/cm.

* * * * *